(12) United States Patent
Chono

(10) Patent No.: US 8,538,103 B2
(45) Date of Patent: Sep. 17, 2013

(54) MEDICAL IMAGE PROCESSING DEVICE, MEDICAL IMAGE PROCESSING METHOD, MEDICAL IMAGE DIAGNOSTIC APPARATUS, OPERATION METHOD OF MEDICAL IMAGE DIAGNOSTIC APPARATUS, AND MEDICAL IMAGE DISPLAY METHOD

(75) Inventor: Tomoaki Chono, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 43 days.

(21) Appl. No.: 13/148,567

(22) PCT Filed: Feb. 2, 2010

(86) PCT No.: PCT/JP2010/051764
§ 371 (c)(1),
(2), (4) Date: Aug. 9, 2011

(87) PCT Pub. No.: WO2010/092918
PCT Pub. Date: Aug. 19, 2010

(65) Prior Publication Data
US 2011/0313291 A1    Dec. 22, 2011

(30) Foreign Application Priority Data

Feb. 10, 2009    (JP) .................................. 2009-027950

(51) Int. Cl.
*G06K 9/00*    (2006.01)
(52) U.S. Cl.
USPC ............ 382/128; 382/130; 382/132; 600/437

(58) Field of Classification Search
USPC ......... 382/128–132; 600/407–429, 437–469, 600/473–480
See application file for complete search history.

(56) References Cited

U.S. PATENT DOCUMENTS

| | | | |
|---|---|---|---|
| 6,535,577 B2* | 3/2003 | Mioitti et al. ................. | 378/155 |
| 7,634,304 B2* | 12/2009 | Falco et al. ................... | 600/424 |
| 7,778,691 B2* | 8/2010 | Zhang et al. ................. | 600/427 |
| 8,009,795 B2* | 8/2011 | Arakita et al. ................... | 378/8 |
| 8,167,802 B2* | 5/2012 | Baba et al. ..................... | 600/437 |
| 2004/0034301 A1* | 2/2004 | Falco ........................... | 600/427 |
| 2009/0275830 A1* | 11/2009 | Falco et al. ................... | 600/437 |

FOREIGN PATENT DOCUMENTS

| | | |
|---|---|---|
| JP | 2002-063564 | 2/2002 |
| JP | 2003-250804 | 9/2003 |
| JP | 2006-247203 | 9/2006 |
| JP | 2007-289720 | 11/2007 |
| JP | 2007-319190 | 12/2007 |

* cited by examiner

*Primary Examiner* — Sanjay Cattungal
(74) *Attorney, Agent, or Firm* — Brundidge & Stanger, P.C.

(57) ABSTRACT

A medical image processing device of the invention includes: an image acquisition unit that acquires three-dimensional image data including a moving organ; an image display unit that displays the three-dimensional image data as a three-dimensional image; an object-to-be-measured setting unit that sets a desired object to be measured on the three-dimensional image displayed on the image display unit; a diagnostic index calculating unit that calculates the amount of displacement of the three-dimensional image data in each time phase for the desired object to be measured and calculates a diagnostic index on the basis of the amount of displacement calculated in each time phase; and a control unit that performs control to display the diagnostic index on the image display unit.

15 Claims, 16 Drawing Sheets

FIG.14
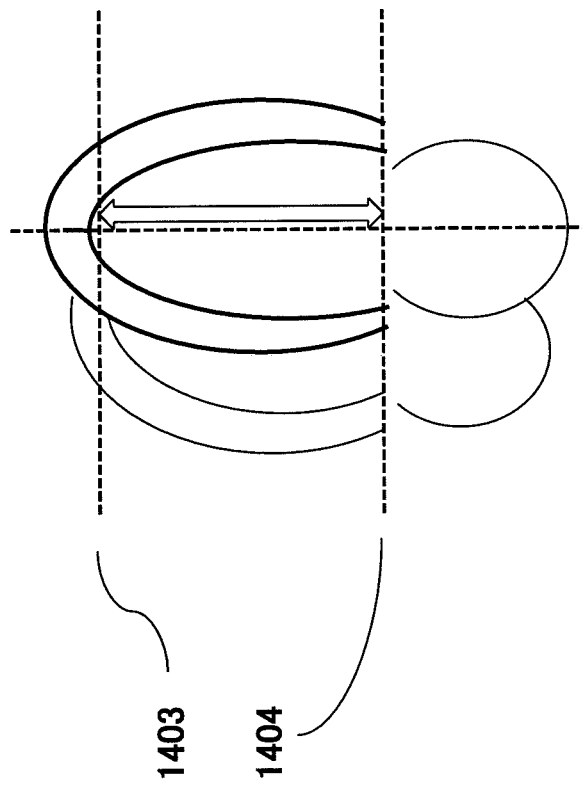
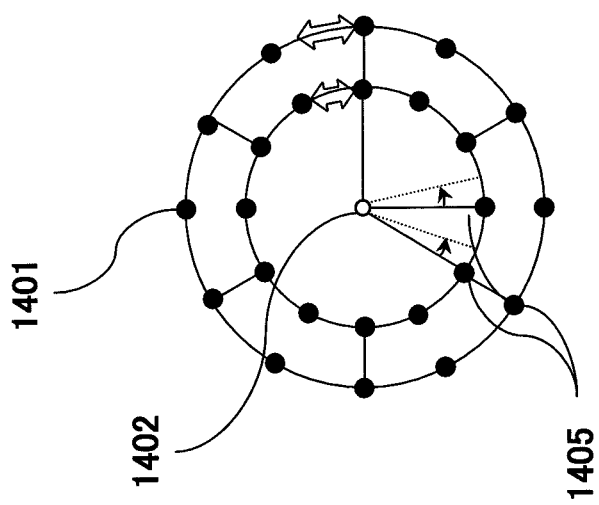
1403
1404
1401
1402
1405

MEDICAL IMAGE PROCESSING DEVICE, MEDICAL IMAGE PROCESSING METHOD, MEDICAL IMAGE DIAGNOSTIC APPARATUS, OPERATION METHOD OF MEDICAL IMAGE DIAGNOSTIC APPARATUS, AND MEDICAL IMAGE DISPLAY METHOD

TECHNICAL FIELD

The present invention relates to a medical image processing device which measures a diagnostic index of a medical image of a moving organ such as the heart, a medical image processing method, a medical image diagnostic apparatus, an operation method of a medical image diagnostic apparatus, and a medical image display method.

BACKGROUND ART

Image diagnosis of a moving organ requires real-time measurement. An ultrasonic diagnostic apparatus is one of the medical image diagnostic apparatuses capable of performing real-time measurement.

In the ultrasonic diagnostic apparatus, an examiner, such as a doctor or a technician for clinical examination, observes a B mode image from which the movement of a moving organ of the subject is acquired over time and diagnoses a disease (myocardial infarction, dilated cardiomyopathy, or the like) of the heart. As an example, an ultrasonic diagnostic apparatus which analyzes the amount of displacement in the movement of the heart in time series in a three-dimensional manner after an examiner sets two specific sections of a cardiac apex image and three specific sections of a short-axis image and calculates a diagnostic index using only the movement data on these sections is known, as in PTL 1.

CITATION LIST

Patent Literature

[PTL 1] JP-A-2007-319190

SUMMARY OF THE INVENTION

Technical Problem

In the conventional technique, however, there is a problem that the examiner cannot calculate a diagnostic index on the desired section because the diagnostic index is calculated only on the fixed section.

Solution to Problem

In order to solve the above-described problem, a medical image processing device of the invention is characterized in that it includes: an image input unit that inputs a plurality of acquired three-dimensional image data including a moving organ in each time phase; a storage unit that stores the plurality of input three-dimensional image data; an image display unit that displays the stored three-dimensional image data as a three-dimensional image; an object-to-be-measured setting unit that sets a desired object to be measured on the three-dimensional image data stored in the storage unit by referring to the three-dimensional image displayed on the image display unit; a diagnostic index calculating unit that calculates the amount of displacement of the three-dimensional image data in each time phase for the desired object to be measured and calculates a diagnostic index on the basis of the amount of displacement calculated in each time phase; and a control unit that performs control to display the calculated diagnostic index on the image display unit.

According to the medical image processing device of the invention described above, the object-to-be-measured setting unit sets a desired object to be measured on the three-dimensional image data stored in the storage unit by referring to the three-dimensional image displayed on the image display unit, the diagnostic index calculating unit calculates the amount of displacement of the three-dimensional image data in each time phase for the desired object to be measured and calculates a diagnostic index on the basis of the amount of displacement calculated in each time phase, and the control unit performs control to display the calculated diagnostic index on the image display unit. Therefore, the examiner can calculate the diagnostic index of the desired object to be measured.

In addition, a medical image processing method of the invention is characterized in that it includes: a first step of inputting a plurality of three-dimensional image data including a moving organ in each time phase by means of an image input unit; a second step of storing the plurality of input three-dimensional image data in a storage unit; a third step of displaying the stored three-dimensional image data as a three-dimensional image on a display unit; a fourth step of setting a desired object to be measured on the three-dimensional image data stored in the storage unit by referring to the three-dimensional image displayed on the image display unit by means of an object-to-be-measured setting unit; a fifth step of calculating the amount of displacement and a diagnostic index of the desired object to be measured from the amount of displacement and a diagnostic index of a reference object to be measured, which is disposed near the desired object to be measured, by means of a diagnostic index calculating unit; and a sixth step of performing control to display the calculated diagnostic index of the desired object to be measured on the image display unit by means of a control unit.

According to the medical image processing method of the invention described above, the three-dimensional image data stored in the storage unit is displayed as a three-dimensional image on the display unit in the third step, a desired object to be measured is set on the three-dimensional image data stored in the storage unit by referring to the three-dimensional image displayed on the image display unit by means of the object-to-be-measured setting unit in the fourth step, the amount of displacement and the diagnostic index of the desired object to be measured are calculated from the amount of displacement and the diagnostic index of the reference object to be measured, which is disposed near the desired object to be measured, by means of the diagnostic index calculating unit in the fifth step, and control to display the calculated diagnostic index of the desired object to be measured on the image display unit is performed by the control unit in the sixth step. Therefore, the examiner can calculate the diagnostic index of the desired object to be measured.

In addition, a medical image diagnostic apparatus of the invention is characterized in that it includes: an image acquisition unit that acquires a plurality of three-dimensional image data including a moving organ in each time phase; a storage unit that stores the plurality of acquired three-dimensional image data; an image display unit that displays the stored three-dimensional image data as a three-dimensional image; an object-to-be-measured setting unit that sets a desired object to be measured on the three-dimensional image data stored in the storage unit by referring to the three-dimensional image displayed on the image display unit; a diagnostic index calculating unit that calculates the amount of displacement and a diagnostic index of the desired object to be measured from the amount of displacement and a diagnostic index of a reference object to be measured which is disposed near the desired object to be measured; and a control unit that performs control to display the calculated diagnostic index of the desired object to be measured on the image display unit.

According to the medical image diagnostic apparatus of the invention described above, the image display unit displays the stored three-dimensional image data as a three-dimensional image, the object-to-be-measured setting unit sets a desired object to be measured on the three-dimensional image data stored in the storage unit by referring to the three-dimensional image displayed on the image display unit, the diagnostic index calculating unit calculates the amount of displacement and the diagnostic index of the desired object to be measured from the amount of displacement and the diagnostic index of the reference object to be measured which is disposed near the desired object to be measured, and the control unit performs control to display the calculated diagnostic index of the desired object to be measured on the image display unit. Therefore, the examiner can calculate the diagnostic index of the desired object to be measured.

In addition, an operation method of a medical image diagnostic apparatus of the invention is characterized in that it includes: a first step of acquiring a plurality of three-dimensional image data including a moving organ in each time phase by means of an image acquisition unit; a second step of storing the plurality of acquired three-dimensional image data in a storage unit; a third step of displaying the stored three-dimensional image data as a three-dimensional image on a display unit; a fourth step of setting a desired object to be measured on the three-dimensional image data stored in the storage unit by referring to the three-dimensional image displayed on the image display unit by means of an object-to-be-measured setting unit; a fifth step of calculating the amount of displacement and a diagnostic index of the desired object to be measured from the amount of displacement and a diagnostic index of a reference object to be measured, which is disposed near the desired object to be measured, by means of a diagnostic index calculating unit; and a sixth step of performing control to display the calculated diagnostic index of the desired object to be measured on the image display unit by means of a control unit.

According to the operation method of the medical image diagnostic apparatus of the invention described above, the stored three-dimensional image data is displayed as a three-dimensional image on the display unit in the third step, a desired object to be measured is set on the three-dimensional image data stored in the storage unit by referring to the three-dimensional image displayed on the image display unit by means of the object-to-be-measured setting unit in the fourth step, the amount of displacement and the diagnostic index of the desired object to be measured are calculated from the amount of displacement and the diagnostic index of the reference object to be measured, which is disposed near the desired object to be measured, by means of the diagnostic index calculating unit in the fifth step, and control to display the calculated diagnostic index of the desired object to be measured on the image display unit is performed by the control unit in the sixth step. Therefore, the examiner can calculate the diagnostic index of the desired object to be measured.

In addition, a medical image display method of the invention is characterized in that it includes: a step of displaying three-dimensional image data including a moving organ as a three-dimensional image on a display unit; a step of setting a desired object to be measured on the three-dimensional image data by referring to the three-dimensional image displayed on the image display unit; a step of calculating the amount of displacement and a diagnostic index of the desired object to be measured from the amount of displacement and a diagnostic index of a reference object to be measured which is disposed near the desired object to be measured; and a step of performing control to display the calculated diagnostic index of the desired object to be measured on the image display unit.

According to the medical image display method of the invention described above, the three-dimensional image data including a moving organ is displayed as a three-dimensional image on the display unit, a desired object to be measured is set on the three-dimensional image data by referring to the three-dimensional image displayed on the image display unit, the amount of displacement and the diagnostic index of the desired object to be measured are calculated from the amount of displacement and the diagnostic index of the reference object to be measured which is disposed near the desired object to be measured, and control to display the calculated diagnostic index of the desired object to be measured on the image display unit is performed. Therefore, the examiner can calculate the diagnostic index of the desired object to be measured.

Advantageous Effects of the Invention

The invention achieves the effects of providing a medical image processing device capable of calculating a diagnostic index of an object that an examiner wants to measure, a medical image processing method, a medical image diagnostic apparatus, an operation method of a medical image diagnostic apparatus, and a medical image display method.

BRIEF DESCRIPTION OF THE DRAWINGS

FIG. 14 is an example of the measurement principle of the ultrasonic image processing device of the fifth embodiment of the invention.

DESCRIPTION OF EMBODIMENTS

Hereinafter, embodiments of the invention will be described in detail.

A medical image processing device of the invention is a section which is responsible for image processing of medical image diagnostic apparatuses, such as an ultrasonic diagnostic apparatus, an X-ray CT apparatus, and an MRI apparatus. In the embodiment of the invention, an ultrasonic image processing device for explaining image processing in an ultrasonic diagnostic apparatus is exemplified. In addition, the invention is not limited to the medical image processing device, and may be extended to various categories starting from the medical image diagnostic apparatus. This extension to various categories will be described later.

First Embodiment

In a first embodiment, a method of extracting the desired local measurement data by acquiring a plurality of three-dimensional image data including a moving organ in advance in each time phase by an ultrasonic image processing device so that the measurement data of the entire heart is obtained in advance will be described using FIGS. 1 to 4.

Figure 1:
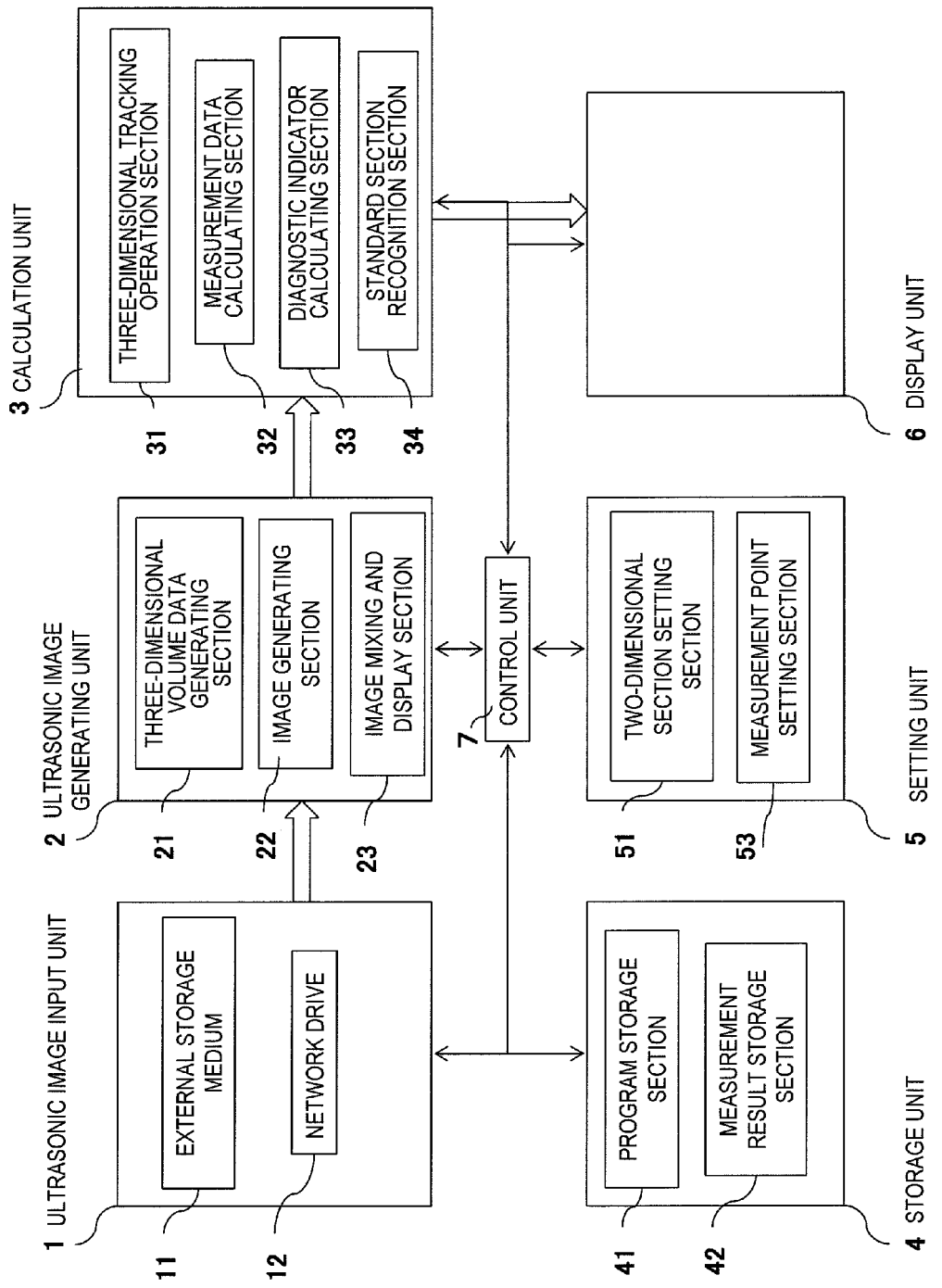
FIG. 1 is an example of a system configuration view of an ultrasonic image processing device of a first embodiment of the invention.
Figure 2:
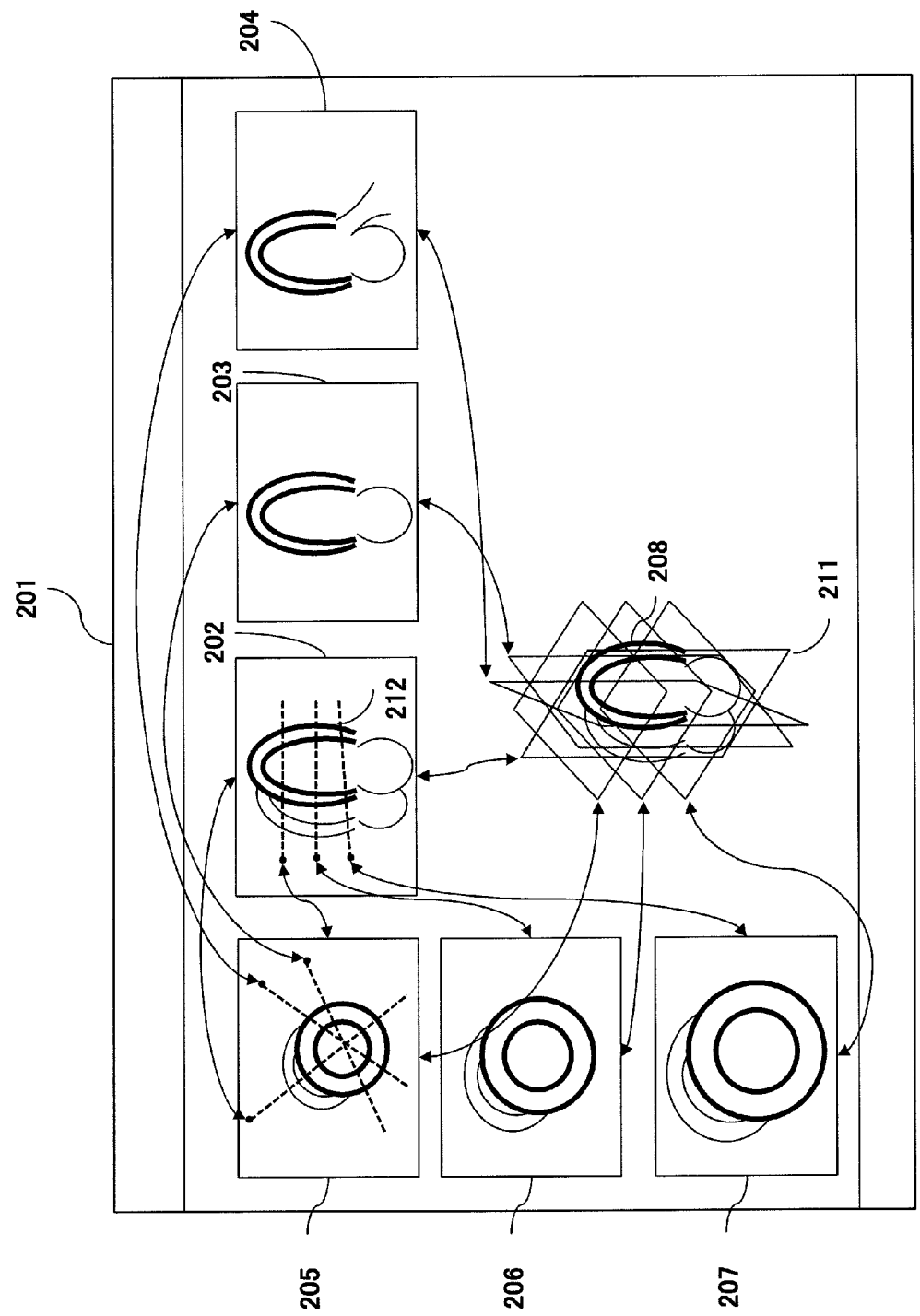
FIG. 2 is an example of a measurement screen of the ultrasonic image processing device of the first embodiment of the invention.
Figure 3:
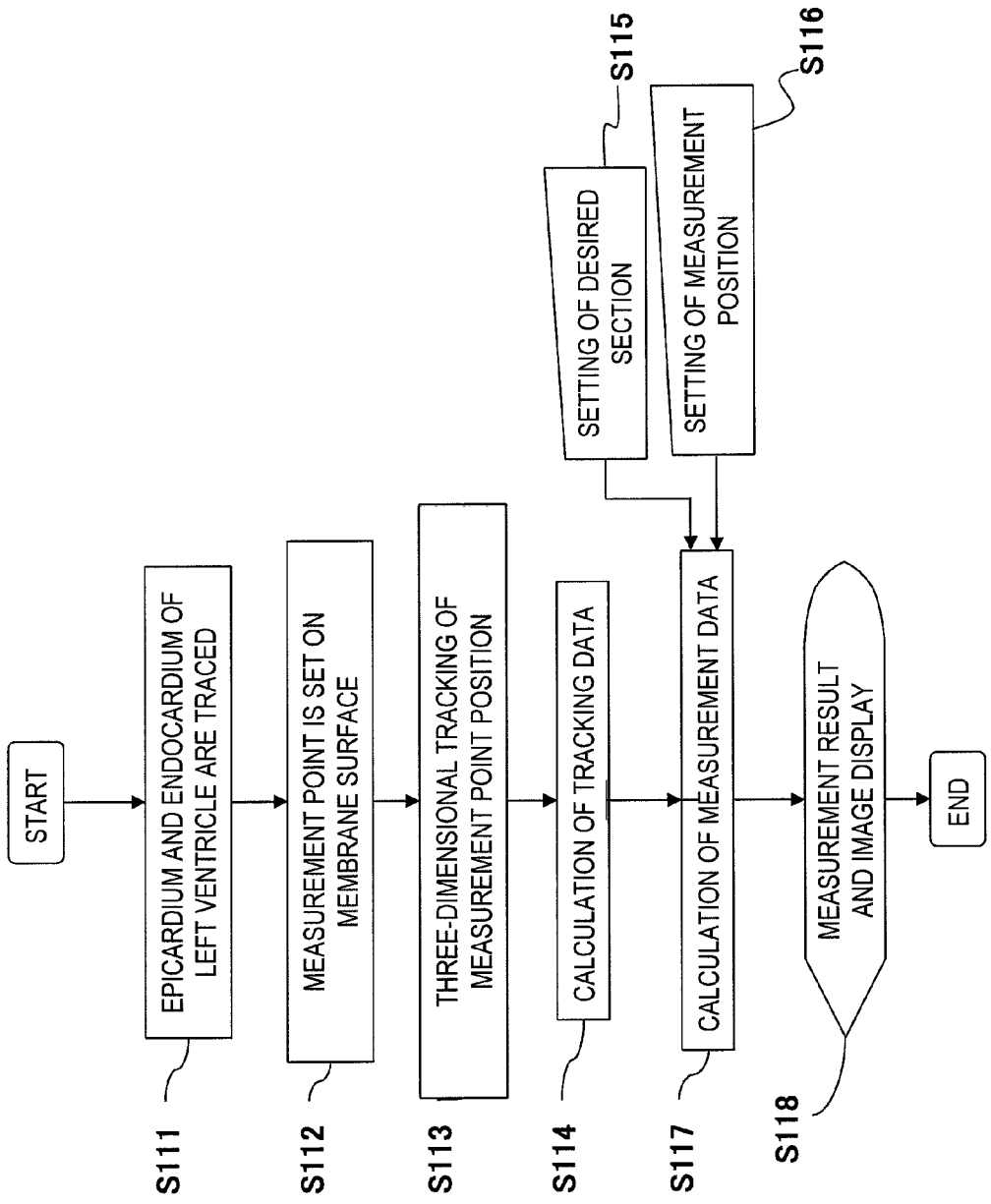
FIG. 3 is a flowchart of measurement processing of the ultrasonic image processing device of the first embodiment of the invention.
Figure 4:
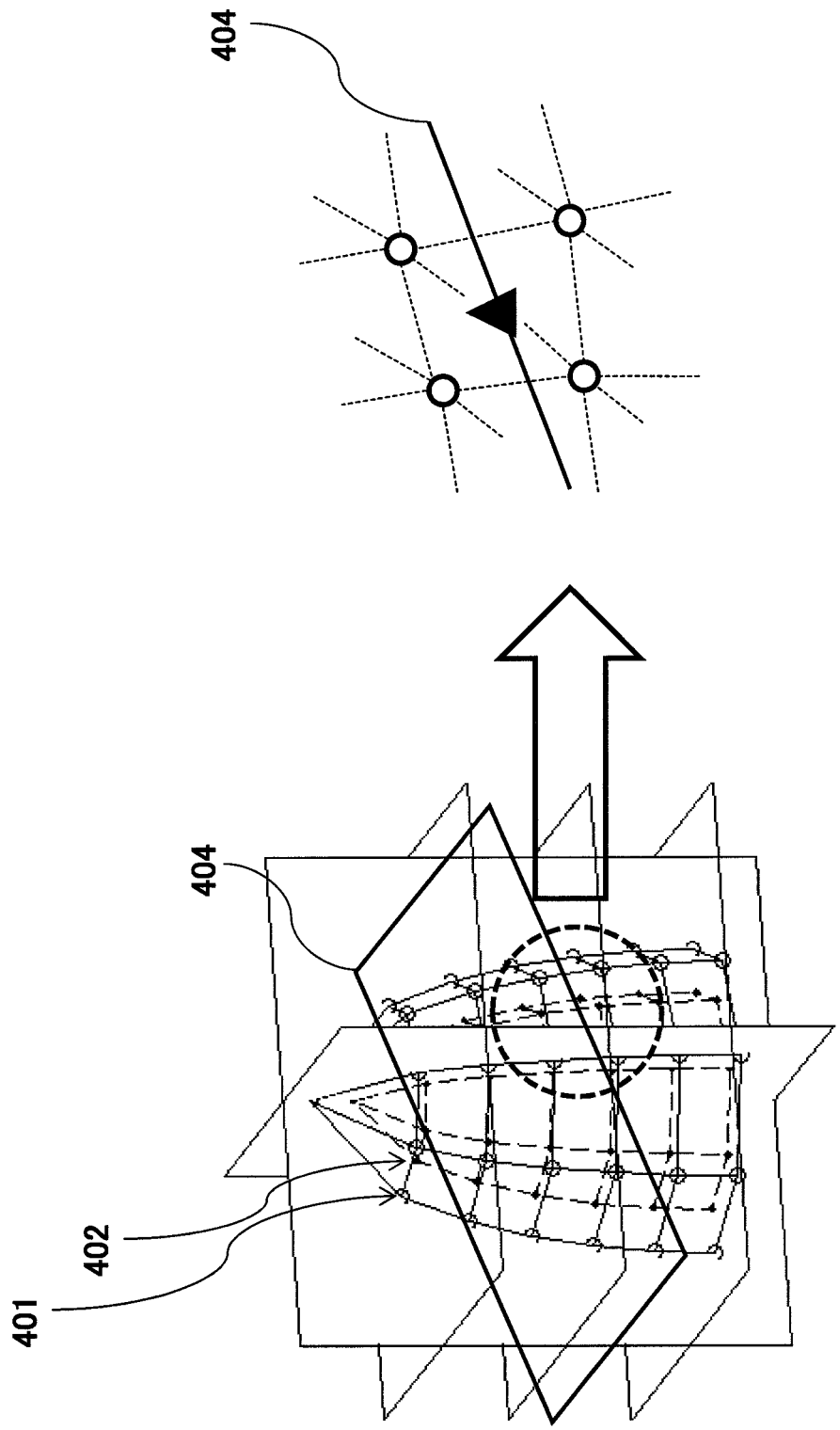
FIG. 4 is a view explaining examples of setting of an object to be measured and calculation of a diagnostic index by the ultrasonic image processing device of the first embodiment of the invention.

FIG. 1 is a view explaining an example of the system configuration of the ultrasonic image processing device of the first embodiment of the invention, FIG. 2 is a view explaining an example of a measurement screen of the ultrasonic image processing device of the first embodiment of the invention, FIG. 3 is a view explaining the flow chart of measurement processing of the ultrasonic image processing device of the first embodiment of the invention, and FIG. 4 is a view explaining examples of setting of an object to be measured and calculation of measurement data by the ultrasonic image processing device of the first embodiment of the invention.

The ultrasonic image processing device includes an ultrasonic image input unit 1, an ultrasonic image generating unit 2, a calculation unit 3, a storage unit 4, a setting unit 5, a display unit 6, and a control unit 7. In the drawing, the solid arrow indicates the flow of control signal data, and the white arrow indicates the flow of image signal data.

The ultrasonic image input unit 1 includes at least one of an external storage medium 11 and a network drive 12, and has a function of inputting an ultrasonic image.

The external storage medium 11 refers to storage media, such as a flexible disk (FD), a magnetic disk, an optical disc, a magneto-optical disc, a USB memory, a ZIP memory, and an SSD memory, in which an ultrasonic image is stored. The external storage medium 11 is inserted if it is a disc and connected if it is a memory so that an ultrasonic image can be read from the computer system.

The network drive 12 makes it possible, for example, in a closed local area network (LAN) in the facilities in a hospital, for an ultrasonic image from a computer system to be read from a server which is installed in the facility and is connected to the LAN. Moreover, in a wide area network (WAN) with communication lines over a wide area, an ultrasonic image from the computer system can be read from an external server connected to the WAN using the network drive 12.

The ultrasonic image generating unit 2 includes a three-dimensional volume data generating section 21, an image generating section 22, and an image mixing and display section 23 and has a function of generating a three-dimensional image and a two-dimensional image from a three-dimensional ultrasonic signal. The three-dimensional volume data generating section 21 generates a three-dimensional image, which is formed by voxel data, from the two-dimensional ultrasonic image input from the ultrasonic image input unit 1 (for example, a three-dimensional image 208 in FIG. 2). When the image input from the ultrasonic image input unit 1 is a three-dimensional image originally, the three-dimensional volume data generating section 21 does not generate a three-dimensional image but outputs the original three-dimensional image. The image generating section 22 generates a two-dimensional image and a three-dimensional image (for example, two-dimensional images 202 to 207 in FIG. 2 in the case of generating a two-dimensional image). The image mixing and display section 23 mixes the three-dimensional and two-dimensional images, a graph or numeric values of a measurement result, and a biological signal such as ECG.

The calculation unit 3 includes a three-dimensional tracking operation section 31, a measurement data calculating section 32, a diagnostic index calculating section 33, and a standard section recognition section 34 and has a function of performing a three-dimensional tracking operation or calculating a diagnostic index. For the three-dimensional tracking operation, the three-dimensional tracking operation section 31 performs a tracking operation using the three-dimensional ultrasonic signal generated by the ultrasonic signal input unit 1 or the three-dimensional image data generated by the ultrasonic image generating unit 2. The tracking operation is to track in time series how much an object-to-be-measured of a subject has been displaced at another time (time phase). The object to be measured indicates at least one of the measurement point (zero-dimensional information) at which an examiner wants to measure, a measurement line (one-dimensional information), a measurement region (two-dimensional information), and a measurement segment (three-dimensional information). In particular, processing of tracking the displacement of a measured image region in the measurement segment (volume data) in each time phase may be called "three-dimensional tracking". The three-dimensional tracking operation section 31 performs an operation of tracking the object to be measured, which is set by the setting unit 5, using three-dimensional image data. As the premise, it is assumed that the tracking operation of measurement data of a reference object to be measured ends and the coordinates or a motion vector of the reference object to be measured is calculated.

As an example of a method of the tracking operation, a method using a three-dimensional cross-correlation operation may be mentioned. The measurement data calculating section 32 calculates the displacement of a measured image region at the desired position as measurement data using the operation result of the three-dimensional tracking operation section 31. For example, when an object to be measured is set at the position other than an object to be measured which is set in advance, the measurement data calculating section 32 calculates the measurement data of a desired object to be actually measured from the measurement data of the reference object to be measured which is present around the object to be measured.

A diagnostic index of an object to be calculated is selected by an examiner using the setting unit 5. The diagnostic index calculating section 33 calculates a diagnostic index, such as strain, from the measurement data of the desired object to be actually measured. For example, the examiner selects a diagnostic index using the setting unit 5, and the diagnostic index calculating section 33 calculates the strain or the rotation angle as a diagnostic index from the measured coordinates or motion vector of the object to be measured. The standard section recognition section 34 recognizes the position of a standard section from the three-dimensional image data stored in the storage unit 4. For example, the standard section recognition section 34 recognizes the standard two-dimensional position from the three-dimensional image data. The standard section is a cardiac apex 2-chamber image, a cardiac apex 4-chamber image, a cardiac apex long-axis image, a parasternal short-axis image, and a parasternal long-axis image which are generally used for measurement. In addition, other than these, the standard section indicates a desired section to be observed for every disease. In addition, when the standard section is defined as a short-axis image, measurement of the myocardium may be based on 16 segments (hereinafter, referred to as "ASE 16 segments") or 17 segments (hereinafter, referred to as "ASE 17 segments") for diagnosis of the myocardium of the heart which is recommended by the American Society of Echocardiography.

The storage unit 4 is a hard disk, a main memory, a cine memory, or the like. The storage unit 4 includes a program storage section 41 and a measurement result storage section 42 as its functional configuration and has a function of storing a calculation program or the result. The program storage section 41 stores a program for controlling the system or operating the calculation unit 3. For example, the program storage section 41 stores a program in which algorithms of a tracking operation, an operation of measurement data, and calculation of a diagnostic index in the calculation unit 3 are stored or a program for controlling each section. The measurement result storage section 42 stores a calculated measurement result. In addition, the storage unit 4 may also be shared with the external storage medium 11 or the network drive 12 of the ultrasonic image input unit 1.

The setting unit 5 serves as a user interface when the examiner sets a measurement position, and has a function of setting a desired measurement position. The setting unit 5 is a keyboard, a mouse, a track ball, a switch, and the like which are input devices necessary for operation of an examiner, and includes a two-dimensional section setting section 51 and a measurement point setting section 53. The two-dimensional section setting section 51 can input an arbitrary position on the desired two-dimensional image that the examiner wants to measure. In response to the input to the two-dimensional section setting section 51, the two-dimensional section setting section 51 sets the read address of the two-dimensional image data in the three-dimensional image data stored in the storage unit 4 by the control unit 7, reads from the storage unit 4 the two-dimensional image data that the examiner wants to observe in the three-dimensional image, and displays it on the display unit 6 (for example, setting of a section 211 displayed on a three-dimensional image in FIG. 2). In response to the input of the position of a desired point that the examiner wants to measure, the measurement point setting section 53 sets the read address of the two-dimensional image data in the three-dimensional image data stored in the storage unit 4 by the control unit 7 and displays a measurement point 212 that the examiner wants to observe on the two-dimensional image on the display unit 6.

The display unit 6 is a display device, such as an LCD monitor, a plasma monitor, or a CRT monitor, and has a function of displaying a measurement result or a diagnostic index (a numeric value, a graph, or the like) and an image. The display unit 6 displays an image mixed by the image mixing and display section 23 and a diagnostic index on the screen.

The control unit 7 serves as a control section of a computer system, such as a CPU, and has a function of controlling the ultrasonic signal input unit 1, the ultrasonic image generating unit 2, the calculation unit 3, the storage unit 4, and the display unit 6 by parameter setting of the examiner to the setting unit 5.

Next, a display example in the first embodiment will be described using FIGS. 2 and 4.

The control unit 7 makes the ultrasonic image generating unit 2 generate a three-dimensional image and displays it on a measurement screen 201 of the display unit 6. The three-dimensional image 208 including a rendering image is displayed on the screen 201. Two-dimensional images 202 to 207 are displayed on the screen 201. The two-dimensional images 202 to 204 and the three-dimensional image 208 will be explained using an image of the heart, which is an example of a moving organ, as an example. The two-dimensional images 202 to 204 are displayed as long-axis images of the heart obtained so as to cut the three-dimensional image 208 in the vertical direction (hereinafter, written as "long-axis images" in abbreviation), and the two-dimensional images 205 to 207 are displayed as short-axis images of the heart obtained so as to cut the three-dimensional image 208 in the horizontal direction (hereinafter, written as "short-axis images" in abbreviation). The two-dimensional images 202 to 207 are matched such that the six sections 211 (dotted lines of the two-dimensional image) in the three-dimensional image 208 are connected by the solid arrows.

In addition, dotted lines on the long-axis image 202 indicate the positions of the three short-axis images 205 to 207, and dotted lines on the short-axis image 205 indicate the positions of the three long-axis images 202 to 204. The dotted line of the long-axis image 202 may also be displayed on the long-axis images 203 and 204, and the dotted line of the short-axis image 205 may also be displayed on the short-axis images 206 and 207. For example, it is assumed that the three long-axis images 202 to 204 are set to cross each other at the angle of 60° in the short-axis image 205 and the three short-axis images 205 to 207 are set in parallel (may not be parallel) in the long-axis image 202 by the examiner using the setting unit 5. Moreover, at the start of display, it is assumed that the three long-axis images 202 to 204 are set to cross each other at the angle of 60° in the short-axis image 205 and the three short-axis images 205 to 207 are set in parallel (may not be parallel) in the long-axis image 202 by the computer program. When the examiner wants to move a desired section, it is manually set using the setting unit 5. In manual setting, the examiner moves a dotted line, which is displayed as at least one section of the six sections 211 in the three-dimensional image 208, using the setting unit 5. Specifically, an examiner can select a long-axis image or a short-axis image on the desired section, like the desired section 404 in FIG. 4, by selecting a section (dotted line) that the examiner wants to move using a mouse and moving the selected dotted line on the screen of the display unit 6. In response to the input of the examiner using the setting unit 5, the control unit 7 operates dotted lines on the screen of the display unit 6, so that the sections (dotted lines) which form the long-axis images 202 to 204 or the short-axis images 205 to 207 move together. Accordingly, the long-axis images 202 to 204 or the short-axis images 205 to 207 change with the moved sections (dotted lines).

Here, the long-axis images 202 to 204 or the short-axis images 205 to 207 are assumed to be standard sections, which are generally imaged by echocardiography, and are also called a cardiac apex 4-chamber section 202, a cardiac apex 2-chamber section 203, a cardiac apex long-axis section 204, a short-axis image cardiac apex level section 205, a short-axis image papillary muscle level section 206, and a short-axis image cardiac base level section 207, respectively. As a two-dimensional image, a standard sectional image of the heart is recognized by a known image recognition technique. Next, the procedure of image recognition will be described briefly. The reference data of a standard image is detected by comparing standard images, such as the cardiac apex 4-chamber section as a standard image template, for example. The standard image template is stored in the storage unit 4. The control unit 7 compares the standard image of the template read from the storage unit 4 with the two-dimensional images cut sequentially from the three-dimensional image, simply calculates a difference between the standard image of the template and each of the two-dimensional images, and determines that the two-dimensional image corresponding to the minimum difference value is most similar to the standard image of the template. In addition, the image recognition technique may be a method of identifying an image by pattern matching, a statistical identification method, a structure identification method, and the like which are other known techniques.

The calculated two-dimensional image is output as a standard image. The long-axis images 202 to 204 or the short-axis images 205 to 207 output in this way may be displayed as initial sections.

Next, an example of specific operations until the initial section is displayed is illustrated.

The control unit 7 makes, the ultrasonic image generating unit 2 generate a three-dimensional image of the heart of the subject and displays the three-dimensional image 208 of the heart on the measurement screen 201 of the display unit 6. The examiner traces the epicardium and the endocardium of the left ventricle on the three-dimensional image of the heart using the setting unit 5. The trace result is shown by heavy line portions on the long-axis images 202 to 204 and the short-axis images 205 to 207 in FIG. 2. For tracing on the three-dimensional image, a known profile extracting method such as a tracing method is applied in which the control unit 7 detects a position, at which a difference between the signal strengths of the epicardium and endocardium and the heart chamber is large, as a boundary position and traces the epicardium and the endocardium automatically using a program of a computer, the examiner inputs a characteristic position, such as the base or apex of the heart, and a contour model based on this is used.

The examiner sets a reference measurement point on the trace surface using the setting unit 5. As will be described in a subsequent step, this reference measurement point becomes a reference point in the tracking operation of a desired measurement point to be set later. The reference measurement point is arrayed at predetermined intervals on the trace surface. Since the time taken for the tracking operation becomes long as a distance between the reference measurement points becomes short and the number of sample points increases accordingly, the examiner sets the desired number of measurement points in a range, which covers the approximately entire trace surface, while checking the time taken for the tracking operation. For example, in FIG. 4, it is possible to set the measurement points at distances therebetween like a white circle mark 401 at the epicardium side of the myocardium and a black circle mark 402 at the endocardium side of the myocardium.

The control unit 7 makes the three-dimensional tracking operation section 31 measure the movement of the reference measurement point by applying a 3D tracking method, which uses a cross-correlation method, to the reference measurement point. Here, the time of the volume is set to t, and the evaluation quantity regarding the amplitude value near the reference measurement point (x, y, z) is set to F(x, y, z). In addition, the amplitude value evaluation quantity of the position (x+u, y+v, z+w) when the time (t+Δt) of the volume has moved by (u, v, and w) within an image after the elapse of Δt is set to F(x+u, y+v, z+w). By changing (u, v, w), the motion vector (u, v, w) when the correlation value S in the following expression becomes a maximum can be detected as the moved position, and it can be set as a motion vector S (u, v, w, t) of the measurement point as shown in Expression 1.

$$S(u, v, w, t) = \sum_{x,y,z} F(x, y, z, t) * F(x+u, y+v, z+w, t+\Delta t)$$ [Expression 1]

Expression 1 is for calculating a motion vector. Other than this, other object movement detection algorithms, such as a Kalman filter or a gradient method, may also be applied. The Kalman filter is an infinite impulse response filter, and the current amount of operation can be acquired if the current amount of observations and the amount of operation in the last time phase are known. The gradient method is a method of estimating a motion vector from the relationship between the spatial brightness gradient of an image and the interframe brightness gradient.

The control unit 7 makes the diagnostic index calculating section 33 perform a tracking operation of the reference measurement point using a motion vector. The diagnostic index of the calculated reference measurement point is a physical quantity, such as a moving speed, strain, and a rotation angle. For example, the moving speed is calculated by time differential of the motion vector described above. The strain is acquired by calculating a change in the distance between measurement points (distortion). In addition, the rotation angle is calculated by resolving the rotational movement of the heart into the movement amounts around the rotary axis.

The examiner sets a desired section on the three-dimensional image 208 using the setting unit 5. An example of the desired section is shown as the desired section 404 in FIG. 4.

The examiner moves a mouse cursor to the display position of a desired measurement point, which the examiner wants to measure on the desired section 404 using a mouse, using the setting unit 5 and presses a mouse button to set the desired measurement point. An example of the desired measurement point is shown as a point shown by the black triangle passing through the desired section 404, as shown in FIG. 4.

A tracking operation of the above desired measurement point is performed from the reference measurement point set above and the result of the tracking operation.

Specifically, the control unit 7 makes the measurement data calculating section 32 calculate the desired measurement point. FIG. 4 also shows an example where a portion (desired measurement point), at which a reference measurement point group (circle mark) and the desired section 404 cross each other, is extracted. Since the desired section 404 including the desired measurement point does not necessarily cross on the measurement point group (circle mark), the position of the desired measurement point shown by the black triangle passing through the desired section 404 should actually be calculated. The method of calculating a desired measurement point is realized by the three-dimensional interpolation operation (also called an interpolation operation) using the measurement data (specifically, the pixel value) of a measurement point group near the triangular point (circle mark). For example, a three-dimensional linear interpolation operation method using eight reference measurement points near the desired measurement points may be used. In this case, the desired measurement point is calculated from the eight neighboring reference measurement points. In addition, when it is necessary to calculate a motion vector of the desired measurement point, it is preferable to calculate it by the interpolation operation using the vector data of the eight reference measurement points near the desired measurement point, for example. Similarly, the control unit 7 calculates a diagnostic index at the desired measurement point by performing an interpolation operation of the diagnostic indexes calculated at the eight neighboring reference measurement points which are disposed with the desired measurement point interposed therebetween.

In addition, other examples of the interpolation operation method of the three-dimensional linear interpolation operation method include a Lagrange interpolation method or a spline interpolation method, and these interpolation methods are superior to the three-dimensional linear interpolation operation method in the calculation accuracy of curve approximation.

The diagnostic index is for evaluating a motor function of the living tissue, such as the wall motion of the heart. Especially for the motor function of the myocardium or the valve, a change in the thickness of a heart wall, speed of the change, strain (distortion) of motion of the heart wall and the strain rate, a rotation angle of the endocardium or epicardium of the heart wall and its speed (rotation speed), relative rotation angles of the endocardium and the epicardium of the heart wall, relative rotation gradients of the endocardium and the epicardium of the heart wall, expansion and contraction of the heart in the long axis direction, strain of the heart in the long axis direction, and the like may be mentioned.

In addition, the broader concept of the interpolation operation described above is that the measurement data calculating section 32 calculates a diagnostic index at the desired measurement point by the weighting operation according to the distance to the reference measurement point.

In addition, as an example of the narrower concept against the broader concept described above, the measurement data calculating section 32 performs an extrapolation operation of a diagnostic index of the desired object to be measured on the basis of the diagnostic indexes of the plurality of set reference objects to be measured. The extrapolation operation is a numeric value estimating method using external division, and the extrapolation point x for external division between the measurement point x1 and the measurement point x2 into m:n is shown in Expression 2.

$$x = x1 + m/(m-n) \times (x2-x1) = (m \times x2 - n \times x1)/(m-n) \quad \text{[Expression 2]}$$

In addition, since the operation accuracy of the extrapolation operation is lower than that of the interpolation operation, the extrapolation operation is used to calculate a diagnostic index of an object to be measured restrictively. For example, when the distance between the measurement point x1 and the measurement point x2 is close, the extrapolation method may be used.

The control unit 7 makes the image mixing and display section 23 perform image mixing of the diagnostic index at the calculated desired measurement point and the two-dimensional image or the three-dimensional image. The control unit 7 displays the numeric value of the diagnostic index, a graph, and an image obtained by pseudo-colorization of the numeric value on the measurement screen 201 of the display unit 6 together with the three-dimensional image, the two-dimensional image, and the biological signal. In addition, the measurement value or the image is stored in the measurement result storage section 42.

An example of the operation in the first embodiment will be described using the flow chart in FIG. 3.

(Step S111)

The control unit 7 makes the ultrasonic image generating unit 2 generate a three-dimensional image of the heart of the subject and displays the three-dimensional image 208 of the heart on the measurement screen 201 of the display unit 6. The examiner traces the epicardium and the endocardium of the left ventricle on the three-dimensional image of the heart using the setting unit 5. The epicardium and the endocardium are shown by the heavy line portions in the long-axis images 202 to 204 and the short-axis images 205 to 207 in FIG. 2. Tracing on the three-dimensional image can be realized by a semi-automatic method. For example, as the semiautomatic tracing method, a known profile extracting method such as a tracing method is applied in which the control unit 7 detects a position, at which a difference between the signal strengths of the epicardium and endocardium and the heart chamber is large, as a boundary position and traces the epicardium and the endocardium automatically, the examiner inputs a characteristic position, such as the base or apex of the heart, and a contour model based on this is used.

(Step S112)

The examiner sets a reference measurement point on the trace surface using the setting unit 5. As will be described in a subsequent step, this reference measurement point becomes a reference point in the tracking operation of a desired measurement point to be set later. The reference measurement point is arrayed at predetermined intervals on the trace surface. Since the time taken for the tracking operation becomes long as a distance between the reference measurement points becomes short and the number of sample points increases accordingly, the examiner sets the desired number of measurement points in a range, which covers the approximately entire trace surface, while checking the time taken for the tracking operation. For example, in FIG. 4, it is possible to set the measurement points at distances therebetween like a white circle mark 401 at the epicardium side of the myocardium and a black circle mark 402 at the endocardium side of the myocardium.

(Step S113)

The control unit 7 makes the three-dimensional tracking operation section 31 measure the movement of the reference measurement point by applying a 3D tracking method to the reference measurement point in the previous step. As the 3D tracking method, it is possible to use a cross-correlation method, for example.

(Step S114)

The control unit 7 makes the diagnostic index calculating section 33 perform a tracking operation of the reference measurement point using a motion vector. The calculated reference measurement point is a physical quantity, such as a moving speed, strain, and a rotation angle. For example, the moving speed is calculated by time differential of the motion vector described above. The strain is acquired by calculating a change in the distance between measurement points (distortion). In addition, the rotation angle is calculated by resolving the rotational movement of the heart into the movement amounts around the rotary axis.

(Step S115)

The examiner sets a desired section on the three-dimensional image 208 using the setting unit 5. An example of the desired section is shown as the desired section 404 in FIG. 4.

(Step S116)

The examiner moves a mouse cursor to the display position of a desired measurement point, which the examiner wants to measure on the desired section 404 using a mouse, using the setting unit 5 and presses a mouse button to set the desired measurement point. An example of the desired measurement point is shown as a point shown by the black triangle passing through the desired section 404, as shown in FIG. 4.

(Step S117)

For the desired measurement point in step S116, a tracking operation is performed from the reference measurement point set in step S112 and the result of the tracking operation.

(Step S118)

The control unit 7 makes the image mixing and display section 23 perform image mixing of the diagnostic index at the calculated desired measurement point and the two-dimensional image or the three-dimensional image. The control unit 7 displays the numeric value of the diagnostic index, a graph, and an image obtained by pseudo-colorization of the numeric value on the measurement screen 201 of the display unit 6 together with the three-dimensional image, the two-dimensional image, and the biological signal. In addition, the measurement value or the image is stored in the measurement result storage section 42.

According to the first embodiment, the examiner can calculate the diagnostic index. In addition, the specific effect of the first embodiment is that the movement of the entire heart is traced first and the reference measurement point is calculated. Accordingly, also when the examiner measures a desired position, the diagnostic index of the desired measurement point is calculated from the reference measurement point. As a result, it is possible to omit the repeated tracking operation performed whenever the desired position is set.

Second Embodiment

In a second embodiment, the procedure of setting an object to be measured at the desired local position of the heart and performing 3D tracking on the set object to be measured in order to calculate the diagnostic index of the object to be measured will be described using FIGS. 1, 2, 4, and 5. Explanation regarding the same sections as in the first embodiment will be omitted.

Figure 5:
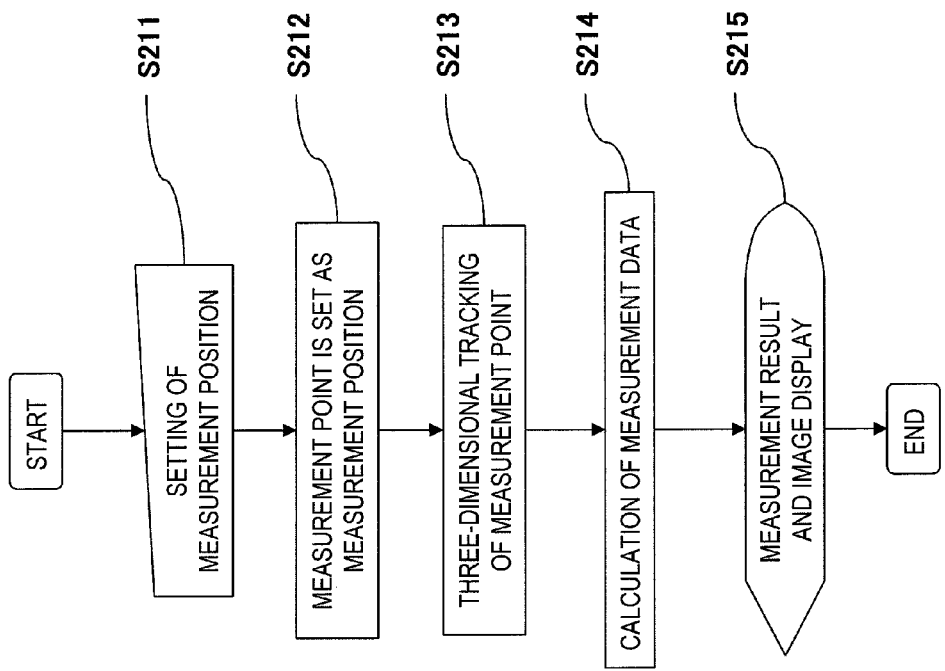
FIG. 5 is a flow chart of measurement processing of an ultrasonic image processing device of a second embodiment of the invention.

FIG. 5 is a flow chart of measurement processing of an ultrasonic image processing device of the second embodiment of the invention.

An example of the operation in the second embodiment will be described using the flow chart in FIG. 5.

(Step S211)

The control unit 7 makes the ultrasonic image generating unit 2 generate a three-dimensional image of the heart of the subject and displays the generated three-dimensional image 208 of the heart on the measurement screen 201 of the display unit 6. Using the setting unit 5, the examiner sets an object to be measured (measurement point) on the myocardial membrane of the long-axis images 202 to 204 and the short-axis images 205 to 207 in FIG. 2 using the setting unit 5. In addition, the examiner sets a heavy line showing the profile of the left ventricle in FIG. 2, a myocardial piece (segment) based on the ASE 17 segments or the like, or a desired measurement point indicating the position of the local tissue, such as the papillary muscle or chorda tendinea, using the setting unit 5.

(Step S212)

The examiner sets a reference object to be measured on the long-axis images 202 to 204 and the short-axis images 205 to 207 in FIG. 2 using the setting unit 5. When the reference object to be measured is a line or a segment, the reference measurement points are further set at predetermined distances therebetween on the line or the outline of the segment. When the reference object to be measured is a point, it is set as a reference measurement point as it is.

(Step S213)

The control unit 7 makes the three-dimensional tracking operation section 31 measure the movement of the reference measurement point by applying 3D tracking to the measurement point set in the previous step.

(Step S214)

The control unit 7 makes the diagnostic index calculating section 33 calculate a diagnostic index at the reference measurement point after the movement.

(Step S215)

The control unit 7 makes the image mixing and display section 23 perform image display of the diagnostic index. As a mode of image display, the numeric value of the diagnostic index, a graph, and an image obtained by pseudo-colorization of the numeric value are displayed on the screen together with the three-dimensional image, the two-dimensional image, and the biological signal. In addition, the measurement value or the image is stored in the measurement result storage section 42.

According to the second embodiment, the examiner can calculate the diagnostic index. In addition, the specific effect of the second embodiment is that the diagnostic index can not be estimated at all the desired positions after the tracking operation, but calculation can be performed in a short time since the calculation is performed only for a local part of the heart. In contrast, since the calculation time is sufficient, it is also possible to increase the measurement accuracy by increasing the density of setting positions of the measurement point.

Third Embodiment

In a third embodiment, the procedure of measuring the relationship of movement between two points will be described using FIGS. 1, 6, and 7, and explanation regarding the same sections as in the first embodiment will be omitted.

Figure 6:
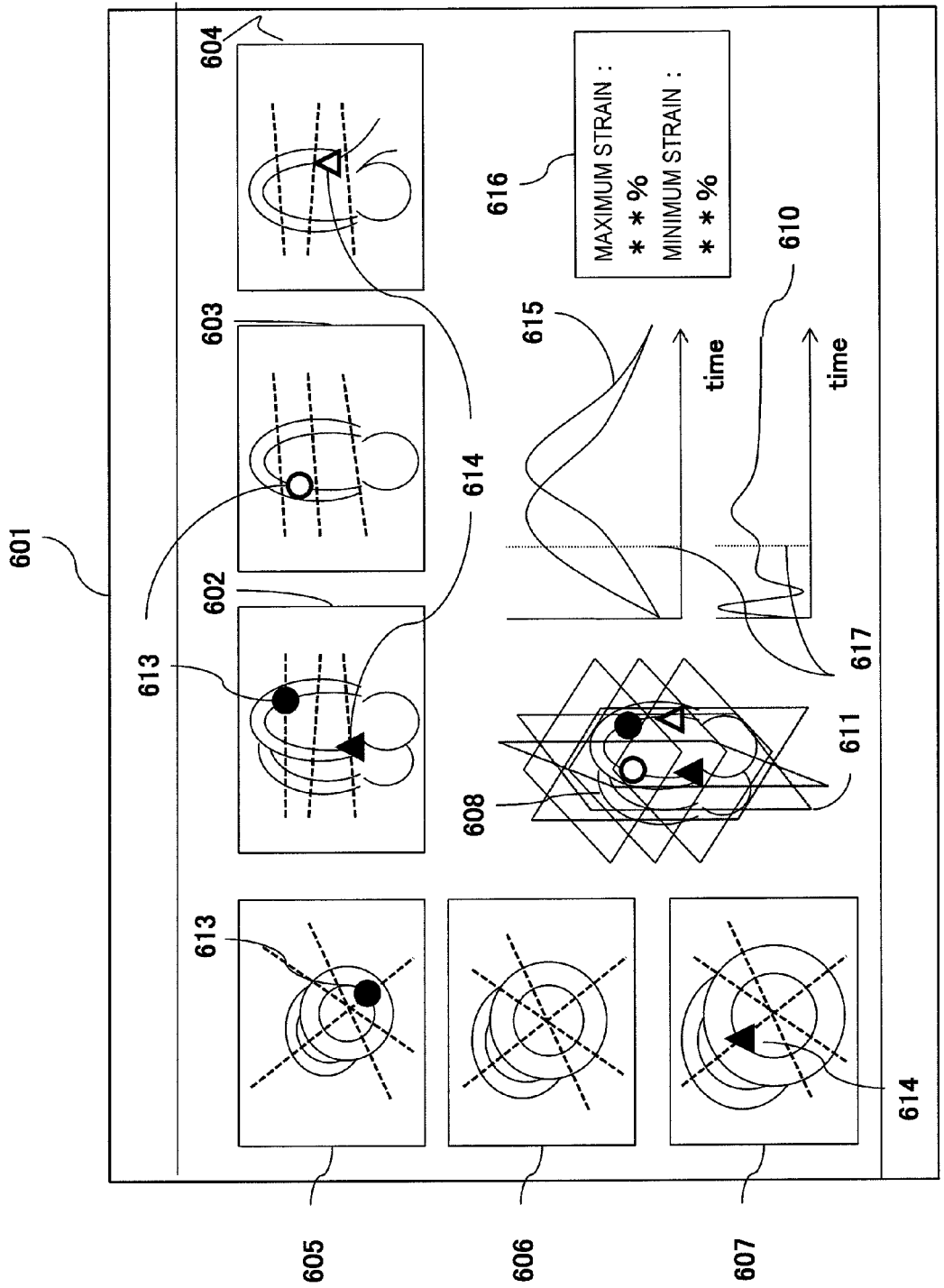
FIG. 6 is an example of a measurement screen of an ultrasonic image processing device of a third embodiment of the invention.
Figure 7:
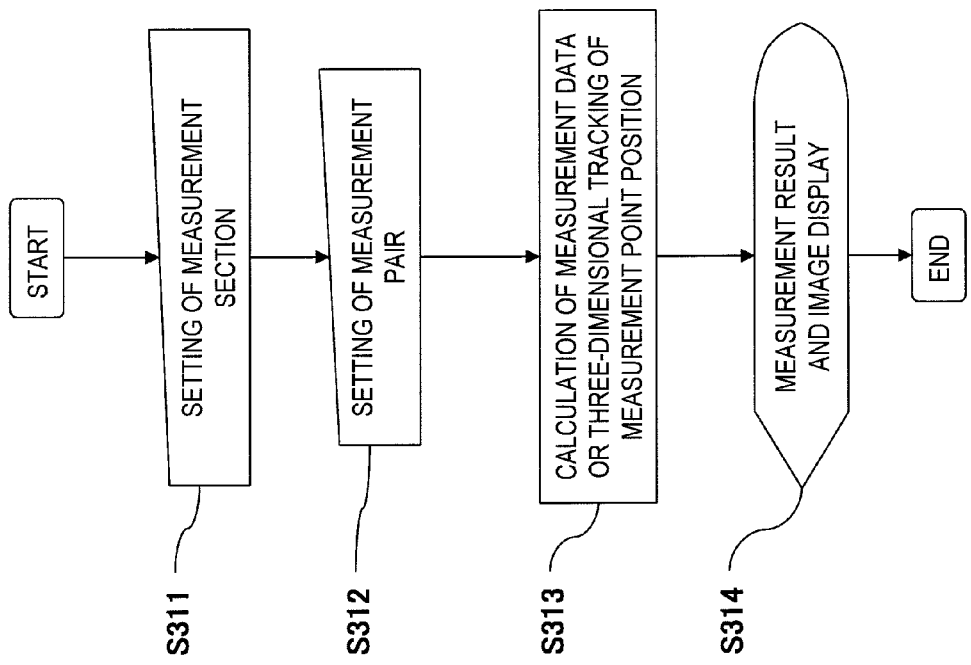
FIG. 7 is a flow chart of the ultrasonic image processing device of the third embodiment of the invention.

FIG. 6 is an example of a measurement screen of an ultrasonic image processing device of the third embodiment of the invention, and FIG. 7 is a flow chart of the ultrasonic image processing device of the third embodiment of the invention.

An example of the operation in the third embodiment will be described using the flow chart in FIG. 7.

(Step S311)

The control unit 7 makes the ultrasonic image generating unit 2 generate a three-dimensional image of the heart of the subject and displays the three-dimensional image 608 of the heart on the measurement screen 601 of the display unit 6. In FIG. 6, an example of measuring a pair 613 of a white circle mark and a black circle mark shown by circle marks and a pair 614 of a white triangle mark and a black triangle mark shown by triangle marks will be described.

(Step S312)

Using the setting unit 5, the examiner sets two desired measurement points at the positions, at which the examiner wants to perform measurement, on any of long-axis images 602 to 604 and the short-axis images 605 to 607 and sets the two points as a pair. For example, it is assumed that the black circle mark 613 is set on the cardiac apex 4-chamber section 602 and the white circle mark 614 is set on the cardiac apex 2-chamber image 603 in FIG. 6. In this case, two points of the black circle mark and the white circle mark are also displayed on the three-dimensional image 608. In addition, since the black circle mark 613 is present on the dotted line which cuts the cardiac apex in the horizontal direction, the black circle mark 613 is also displayed on the short-axis image cardiac apex level section 605 showing a cross-section on this dotted line.

Thus, the control unit 7 makes a control such that if a desired measurement point is set, the desired measurement point is also displayed at the corresponding point, which matches the display image on which the desired measurement point is set, on the other images on which the measurement point is not set. The left of the black triangle mark 614 which is another measurement pair is also similarly set on the cardiac apex 4-chamber section 602, and the black triangle mark 614 is also displayed on the short-axis image cardiac base level section 607 on the dotted line.

(Step S313)

In the case of the first embodiment, the control unit 7 makes the measurement data calculating section 32 calculate a diagnostic index of the positions of two points from the tracking result already obtained. Moreover, in the case of the second embodiment, the control unit 7 makes the three-dimensional tracking operation section 31 perform the 3D tracking operation of two measurement points and the diagnostic index calculating section 33 calculate a diagnostic index. As the diagnostic index for measurement between two points, a distance between two points, strain of the movement of the heart, a strain rate, and the like are calculated.

(Step S314)

The control unit 7 makes the image generating section 22 generate the graph data of a graph 615, in which the calculated diagnostic index is set on the vertical axis and the horizontal axis is set as a time axis, and displays the generated graph data on the display unit 6. In addition, the control unit 7 displays the diagnostic index as a measurement value 616 on the screen 601. Although the maximum strain xx % and the minimum strain xx % are illustrated herein, any value such as a distance between two points, a strain rate, and an average strain rate may be used as long as it is measured or calculated data regarding the distance between two points or the strain value. In addition, the control unit 7 may display a biological signal 610, such as an electrocardiographic wave, together on the screen 601 of the display unit 6. The control unit 7 controls these data items including the three-dimensional image and the two-dimensional image such that if there is one change element, it is reflected on each display element. When displaying a time phase cursor 617 on the graph 615, the control unit 7 displays it on the screen 601 of the display unit 6 in synchronization with the time phase of the three-dimensional image and the two-dimensional image which are currently displayed.

According to the third embodiment, the examiner can calculate the diagnostic index. In addition, the specific effect of the third embodiment is that the measurement position of a point is easily set by providing a user interface, which can be set on the two-dimensional image, even in the measurement on the three-dimensional image.

Fourth Embodiment

In a fourth embodiment, the procedure of observing the movements of ASE 17 segments of the myocardium will be described using FIGS. 8 to 11, and explanation regarding the same sections as in the first embodiment will be omitted.

Figure 8:
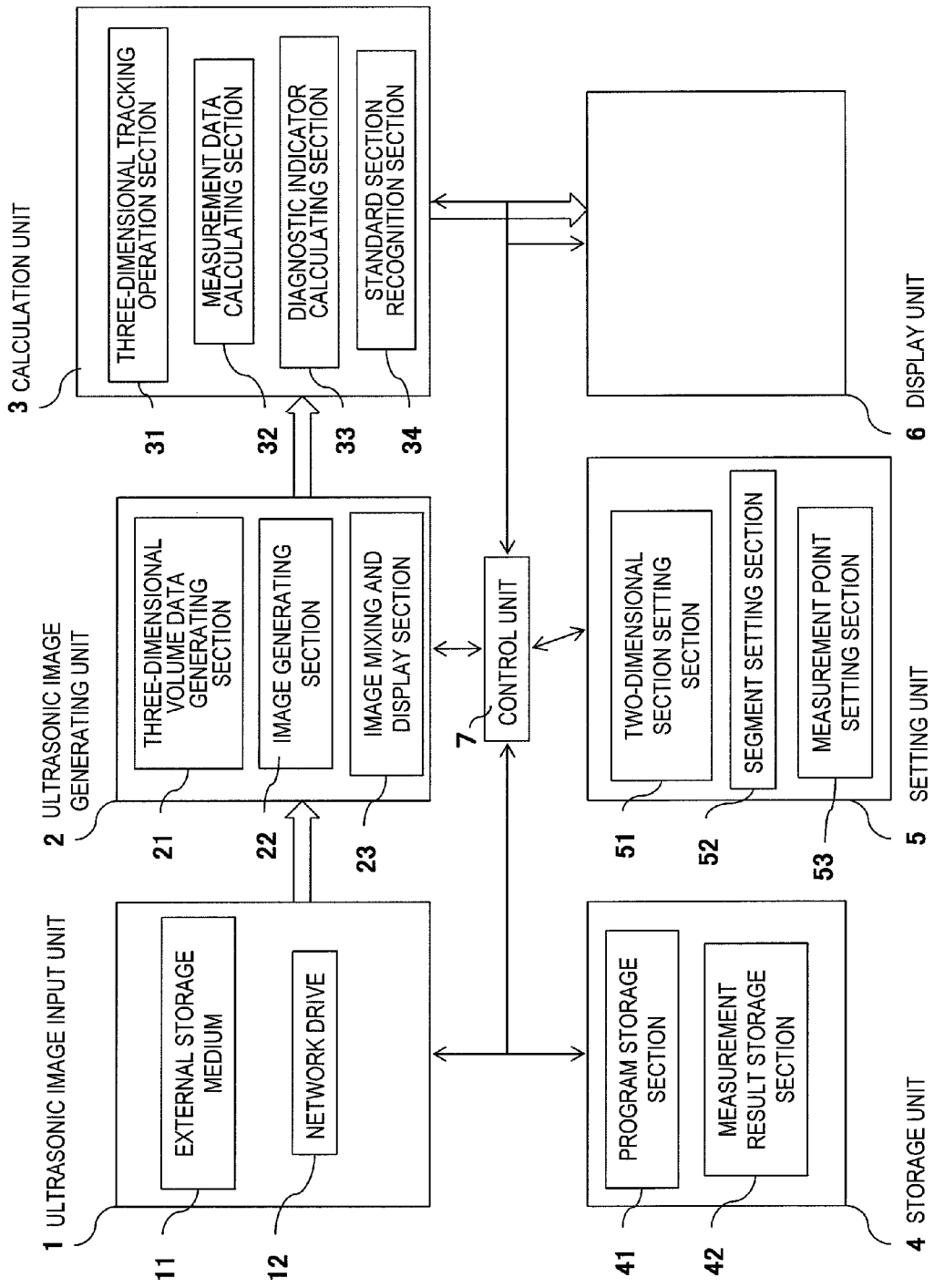
FIG. 8 is an example of a system configuration view of an ultrasonic image processing device of a fourth embodiment of the invention.
Figure 9:
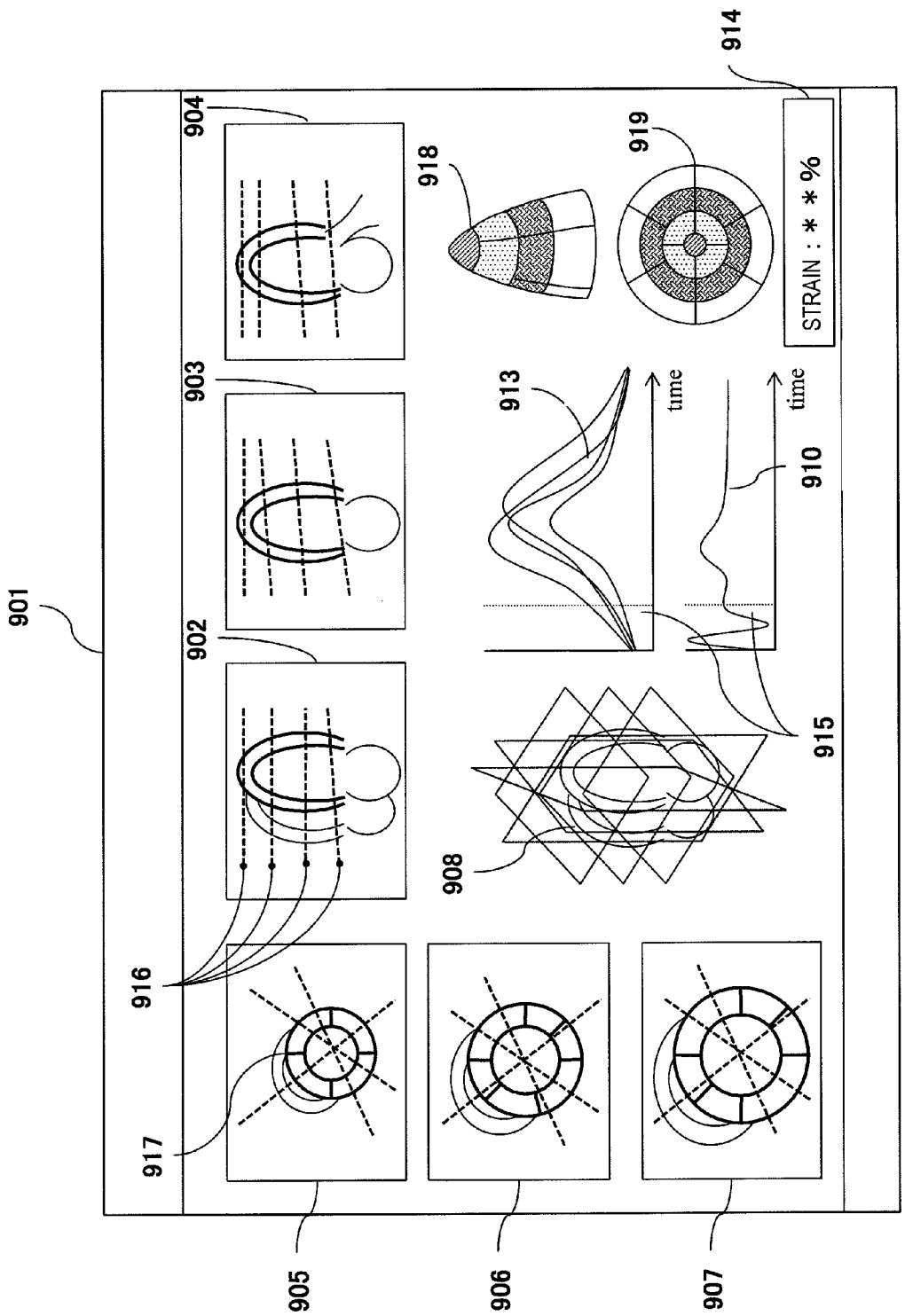
FIG. 9 is an example of a measurement screen of the ultrasonic image processing device of the fourth embodiment of the invention.
Figure 10:
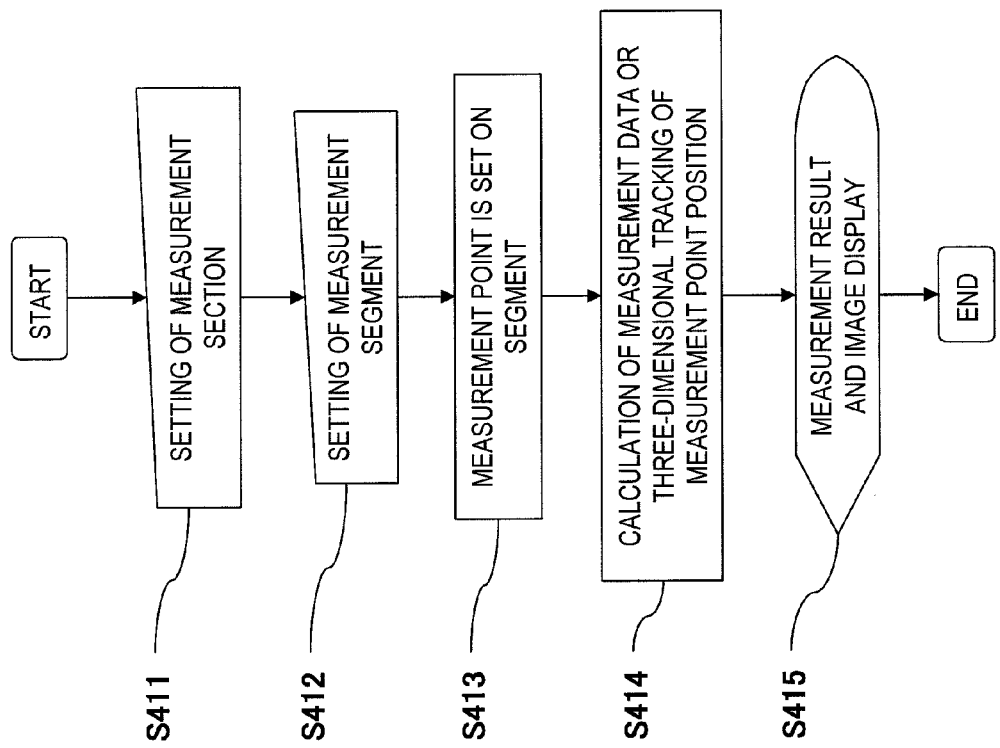
FIG. 10 is a flow chart of measurement of the ultrasonic image processing device of the fourth embodiment of the invention.
Figure 11:
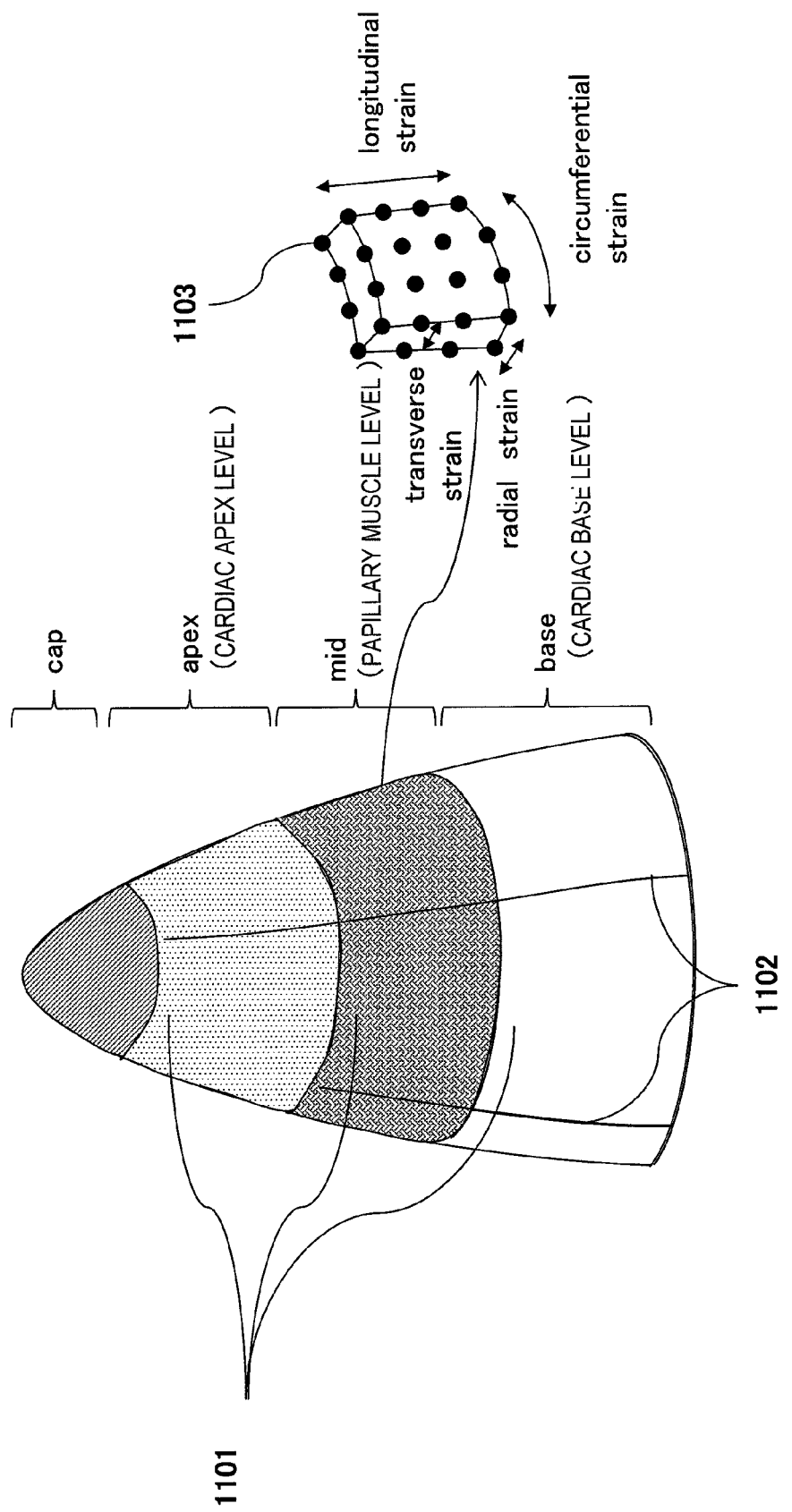
FIG. 11 is an example of the measurement principle of the ultrasonic image processing device of the fourth embodiment of the invention.

FIG. 8 is an example of the system configuration of an ultrasonic image processing device of the fourth embodiment of the invention, FIG. 9 is an example of a measurement screen of the ultrasonic image processing device of the fourth embodiment of the invention, FIG. 10 is a flow chart of measurement of the ultrasonic image processing device of the fourth embodiment of the invention, and FIG. 11 is an example of the measurement principle of the ultrasonic image processing device of the fourth embodiment of the invention.

In the fourth embodiment, a segment setting unit 52 is added to the setting unit 5 in the first embodiment. The segment setting unit 52 performs setting for dividing the heart into myocardial pieces (segments) (dotted line 916 showing the cut surface displayed on long-axis images 902 to 904 and short-axis image 905 to 907 in FIG. 9). For example, the segment setting unit 52 is an interface which sets the boundary for dividing the myocardium of the left ventricle into regions based on the ASE 17 segments on the displayed short-axis image (setting of the dotted line 916 or the solid line 917 displayed on the long-axis images 902 to 904 and the short-axis images 905 to 907 in FIG. 9).

An example of the operation in the fourth embodiment will be described using the flow chart in FIG. 10.

(Step S411)

The control unit 7 makes the ultrasonic image generating unit 2 generate a three-dimensional image of the heart of the subject and displays the three-dimensional image of the heart on a measurement screen 901 of the display unit 6. Setting the segments on the object to be measured is to set the boundary of segments on the two-dimensional image more simply than in manual setting of the examiner. Accordingly, it becomes possible to eliminate the setting effort compared with the manual setting.

The examiner sets a segment, which is an object to be measured, using the two-dimensional section setting section 51. Here, since a segment should be set, the control unit 7 controls the long-axis images 902 to 904 and the short-axis image 905 to 907 in FIG. 9 in the same manner as in the first embodiment, so that a cardiac apex 4-chamber image 902, a cardiac apex 2-chamber image 903, a cardiac apex long-axis image 904, a short-axis image cardiac apex level lower end (apex) 905, a short-axis image papillary muscle level lower end (mid) 906, and a short-axis image cardiac base level lower end (base) 907 are displayed.

(Step S412)

The control unit 7 divides the myocardium into 17 segments by the segment setting unit 52. If the myocardium is shown in a three-dimensional way in FIG. 11, it is divided into four levels of cap, apex, mid, and base by horizontal parting lines 1101. In addition, base and mid are divided into 6 parts and apex is divided into 4 parts by vertical parting lines 1102. In order to set these, the examiner sets the dotted line 1101 for horizontal division on the long-axis images 902 to 904 and the short-axis images 905 to 907 of the setting screen in FIG. 9 using the setting unit 5. This dotted line 1101 is displayed on the short-axis images 905 to 907. In addition, on the short-axis images 905 to 907, a solid line 1102 which traverses the myocardium in order to divide it in the vertical direction is set.

(Step S413)

The examiner sets a measurement point on the segment using the measurement point setting section 53. Reference numeral 1103 in FIG. 11 is a view obtained by extracting one segment of a mid portion of a three-dimensional view at the left side of the same drawing, and this is set as a measurement point. The measurement points 1103 are automatically set at appropriate distances therebetween on the boundary of the segment or the surface, so that the movement of the entire segment can be measured.

(Step S414)

In the case of the first embodiment, the control unit 7 makes the measurement data calculating section 32 calculate the measurement data of the set measurement points from the tracking result already obtained. Moreover, in the case of the second embodiment, the control unit 7 makes the three-dimensional tracking operation section 31 perform the 3D tracking operation of the set measurement points and the diagnostic index calculating section 33 calculate the measurement data. As the measurement data of strain, longitudinal strain along the longitudinal (vertical) direction of the pericardial surface, circumferential strain along the circumferential direction, radial strain along the central axis direction of the heart, transverse strain along a direction perpendicular to the pericardial surface, and the like are calculated for each segment.

(Step S415)

The control unit 7 makes the ultrasonic image generating unit 2 calculate the above calculated diagnostic index to make an image or a graph and displays the long-axis images 902 to 904, the short-axis images 905 to 907 or a three-dimensional image 908, and a graph 913 on the display unit 6. In addition, a biological signal 910, such as an electrocardiographic wave or a heart sound wave, may also be displayed. The diagnostic index curve of ASE 17 segments is displayed so as to overlap the graph 913. The three-dimensional image 918 displayed separately from the three-dimensional image 908 is for mapping the diagnostic index of a segment on the two-dimensional image by pseudo-colorization (color change). In addition, a bull's eye image 919 is for observing the myocardium by creating a two-dimensional plan view for the three-dimensional image 918. In addition, the numeric value of the strain of each segment is displayed in a table form 914.

According to the fourth embodiment, the examiner can calculate the diagnostic index. In addition, the specific effect of the fourth embodiment is that the size or timing of the movement in each place of the myocardium can be quantitatively evaluated since the movements of the ASE 17 segments of the myocardium can be simultaneously observed, and it is possible to provide the useful information for diagnosis accordingly. For example, if a strain value is mapped on the three-dimensional image 918 or the bull's eye image 919, coloring according to contraction and expansion of the myocardium is performed. This helps to allow grasping of the movement of the myocardium at a glance.

Fifth Embodiment

In a fifth embodiment, the procedure of measuring a temporal change in the rotation angle of the heart on a desired section will be described using FIGS. 8 and 12 to 14, and explanation regarding the same sections as in the first embodiment will be omitted.

Figure 12:
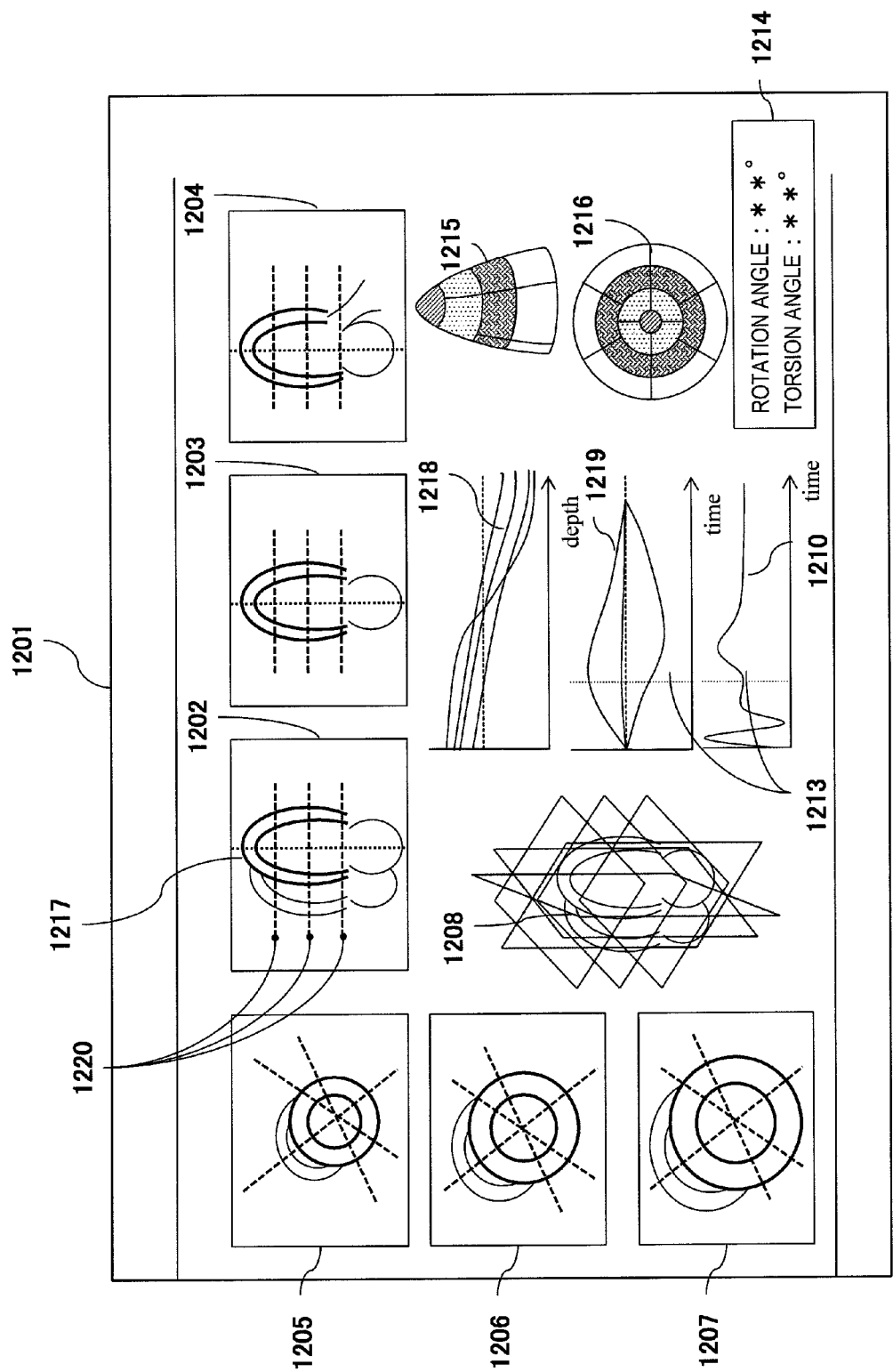
FIG. 12 is an example of a measurement screen of an ultrasonic image processing device of a fifth embodiment of the invention.
Figure 13:
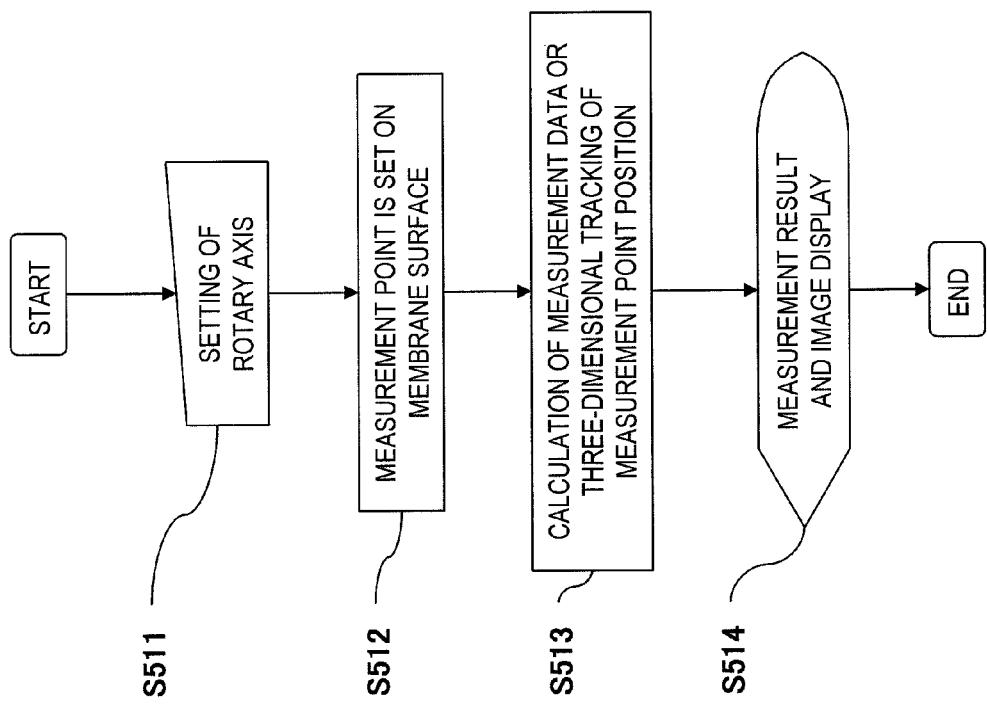
FIG. 13 is a flow chart of the ultrasonic image processing device of the fifth embodiment of the invention.

FIG. 12 is an example of a measurement screen of an ultrasonic image processing device of the fifth embodiment of the invention, FIG. 13 is a flow chart of the ultrasonic image processing device of the fifth embodiment of the invention, and FIG. 14 is an example of the measurement principle of the ultrasonic image processing device of the fifth embodiment of the invention.

For the heart, it is known that the cardiac apex and the cardiac base rotate in the opposite directions with the long axis direction as an axis so that the heart moves so as to be twisted. This twisting, that is, a rotational movement analysis is also considered to be an index useful for diagnosis.

An example of the operation in the fifth embodiment will be described using the flow chart in FIG. 13.

(Step S511)

The control unit 7 makes the ultrasonic image generating unit 2 generate a three-dimensional image of the heart of the subject and displays the three-dimensional image of the heart on a measurement screen 1201 of the display unit 6. The examiner sets a rotary axis 1217 (dotted line) for measuring the rotation on long-axis images of long-axis images 1202 to 1204. In addition, the examiner performs setting using the setting unit 5 so as to pass the center of the cardiac base from the cardiac apex. A line perpendicular to this is displayed as 1220 (dotted line), and a section determined by these is displayed on short-axis images 1205 to 1207.

(Step S512)

The examiner sets a measurement point on the membrane surface using the measurement point setting section 53. Any of the short-axis images 1205 to 1207 perpendicular to the rotary axis 1217 in FIG. 12 shows that it rotates along the white arrow. In the case of the second embodiment, the control unit 7 sets a measurement point 1401 on the short-axis images 1205 to 1207. The examiner arrays the measurement points so that the entire membrane surface can be measured. In FIG. 14, the measurement points are uniformly arrayed.

In addition, in the case of the first embodiment, the control unit 7 makes the measurement data calculating section 32 calculate a diagnostic index of the intersection 1401 between the section perpendicular to the rotary axis and the membrane surface using the diagnostic index of the measurement point set already. In this case, the diagnostic index can be calculated continuously by moving the section from the cardiac apex 1101 to the cardiac base 1102 along the rotary axis.

(Step S513)

In the case of the second embodiment, the control unit 7 makes the three-dimensional tracking operation section 31 perform the 3D tracking operation of the set measurement points and the diagnostic index calculating section 33 calculate the diagnostic index. In this case, since the measurement point is set only on the short-axis images 1205 to 1207, the rotation angles of only the three sections are calculated.

As the rotation angle, it is preferable to calculate the rotation angle of each point around the central axis like the rotation angle 1405 in FIG. 14. In addition, the average value of the rotation angles of the respective measurement points on the entire membrane surface may also be calculated as an average rotation angle of the section. In addition, it is also possible to calculate a difference from the rotation angle of a certain section using the rotation angle of the certain section as a reference.

(Step S514)

The control unit 7 makes the ultrasonic image generating unit 2 calculate the above calculated diagnostic index to make an image or a graph and displays the long-axis images 1202 to 1204, the short-axis images 1205 to 1207 or a three-dimensional image 1208, and a graph 1218 on the display unit 6. In addition, a biological signal 1210, such as an electrocardiographic wave, is displayed. The graph may express a temporal change 1219 in the rotation angle of each section with respect to the time axis. In addition, the rotation angle of each segment can be calculated by setting a segment using the interface in the third embodiment. In the same manner as in the third embodiment, this can be displayed by mapping onto a three-dimensional image 1215 or a bull's eye image 1216 by pseudo-colorization. These data items are displayed in synchronization with the three-dimensional image 1208, the long-axis images 1202 to 1204, and the short-axis images 1205 to 1207. A time phase cursor 1213 on the graph moves in synchronization with the time phase of an image. In the case of the first embodiment, the rotation angle can be calculated continuously from the cardiac apex to the cardiac base. Accordingly, a change according to the depth of the rotation angle is displayed as a graph 1218 using the depth on the axis as an axis. In addition, the rotation angle or the torsion angle is displayed as numeric values at the position shown by reference numeral 1214 on the screen.

According to the fifth embodiment, the examiner can calculate the diagnostic index. In addition, the specific effect of the fifth embodiment is that a temporal change in the rotation angle of the heart on a desired section can be measured. In addition, since a change in the rotation angle which is spatially continuous along the rotary axis can also be observed, it becomes possible to analyze the movement of the heart in more detail.

Sixth Embodiment

In a sixth embodiment, the procedure of performing measurement by setting the position of the section using a disease name list will be described using FIGS. 8, 15, and 16, and explanation regarding the same sections as in the first embodiment will be omitted.

Figure 15:
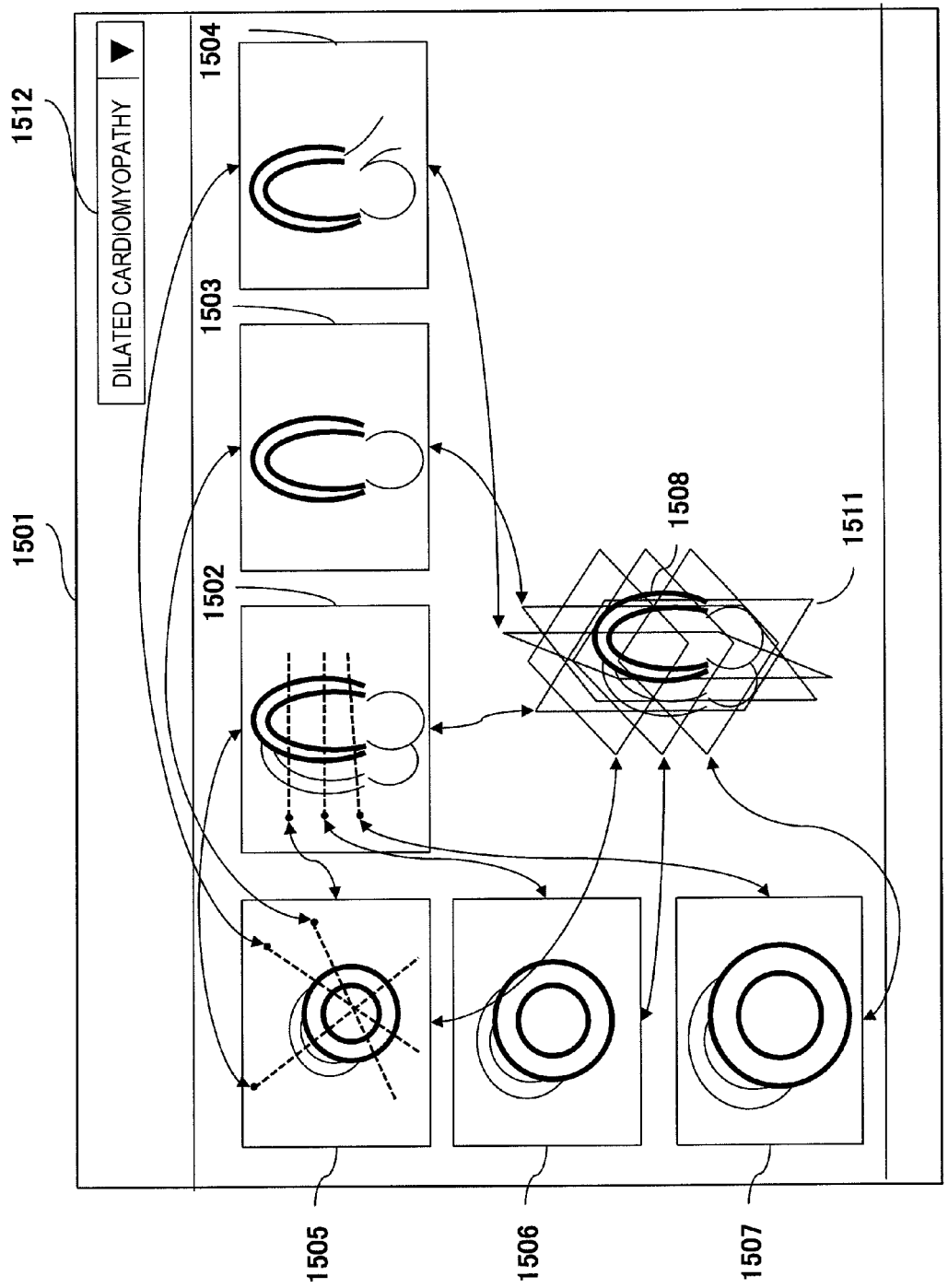
FIG. 15 is an example of a measurement screen of an ultrasonic image processing device of a sixth embodiment of the invention.
Figure 16:
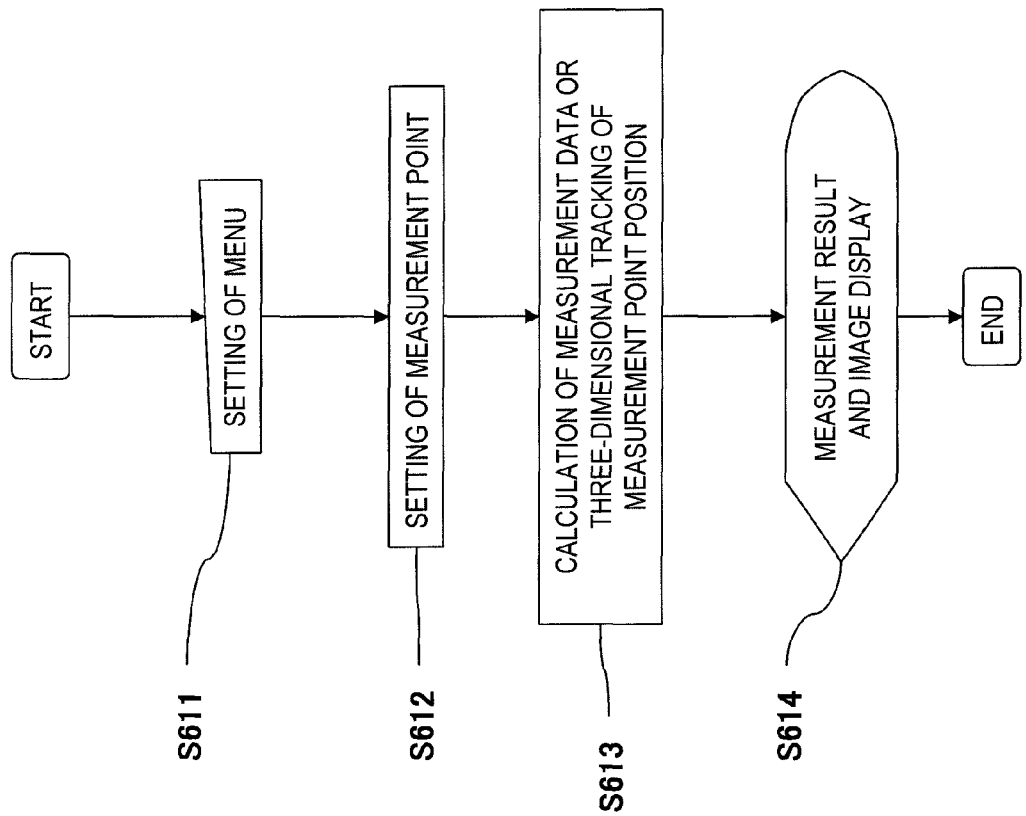
FIG. 16 is a flow chart of the ultrasonic image processing device of the sixth embodiment of the invention.

FIG. 15 is an example of a measurement screen of an ultrasonic image processing device of the sixth embodiment of the invention, and FIG. 16 is a flow chart of the ultrasonic image processing device of the sixth embodiment of the invention.

An example of the operation in the sixth embodiment will be described using the flow chart in FIG. 16.

(Step S611)

The control unit 7 makes the ultrasonic image generating unit 2 generate a three-dimensional image of the heart of the subject and displays the three-dimensional image of the heart on a measurement screen 1501 of the display unit 6. The examiner sets the position of the section in a disease name list 1512. The shape or the movement of the heart differs between diseases. Accordingly, disease names are listed in advance on the disease name list 1512. If a disease name is selected from the list, the information regarding the position of the section measured in the disease is read from the storage unit 4, and the positions of dotted lines and long-axis images 1502 to 1504 and short-axis images 1505 to 1507 are set.

(Step S612)

The examiner sets a desired measurement point on the measurement screen 1501 of the display unit 6 using the measurement point setting section 53.

(Step S613)

In the case of the second embodiment, the control unit 7 makes the three-dimensional tracking operation section 31 perform the 3D tracking operation of the set measurement points and the diagnostic index calculating section 33 calculate the diagnostic index.

(Step S614)

The control unit 7 makes the ultrasonic image generating unit 2 calculate the above calculated diagnostic index to make an image or a graph and displays the long-axis images 1502 to 1504 and the short-axis images 1505 to 1507 or a three-dimensional image 1508 on the display unit 6.

According to the sixth embodiment, the examiner can calculate the diagnostic index. In addition, the specific effect of the sixth embodiment is that a list can be made on the basis of shape abnormalities, such as dilated cardiomyopathy or hypertrophic cardiomyopathy, or a list can be made on the basis of movement abnormalities by showing a name of an infarction part, for example. Then, it is also possible to perform fine adjustment of the position of the section manually later if necessary.

Although the medical image processing device has been described in each embodiment, the medical image processing device may be considered as the invention of a medical image diagnostic apparatus if an image acquisition unit that acquires a plurality of three-dimensional image data including a moving organ in each time phase is added.

The image acquisition unit (ultrasonic signal generating unit) is replaced with the image input unit 1, and the ultrasonic signal generating unit has a following configuration.

The ultrasonic signal generating unit includes an ultrasonic probe and an ultrasonic signal transmitting and receiving section, and has a function of acquiring a three-dimensional ultrasonic signal.

The ultrasonic probe has a linear type scanning method, a convex type scanning method, a sector type scanning method, and the like, and is formed by arraying vibrator elements capable of transmitting and receiving an ultrasonic wave at least in a one-dimensional direction. The ultrasonic probe is used in contact with the subject so that an ultrasonic signal of the subject can be acquired by transmission and reception of an ultrasonic wave. A 2D array probe is mentioned as an example of the ultrasonic probe. The 2D array probe is formed by arraying vibrator elements capable of transmitting and receiving an ultrasonic wave in a two-dimensional direction, and can acquire a three-dimensional ultrasonic signal of the subject by one-time transmission and reception of an ultrasonic wave.

In addition, the same function as the 2D array probe can also be realized by a 1D array probe. The 1D array probe has a linear type scanning method, a convex type scanning method, a sector type scanning method, and the like, and is formed by arraying vibrator elements capable of transmitting and receiving an ultrasonic wave in a one-dimensional direction. The 1D array probe can be made to operate in substantially the same manner as the 2D array probe by the following operation. The operation is to move the 1D array probe in a direction, which is approximately perpendicular to the arrangement direction of vibrators of the 1D array probe, while bringing it into contact with the subject. The 1D array probe may be made to move by manual operation of the examiner or by mechanical operation. The mechanical operation is to acquire a three-dimensional ultrasonic image by swinging an ultrasonic probe, which scans a two-dimensional tomographic surface with an ultrasonic signal, in a direction perpendicular to the two-dimensional tomographic surface, for example, as disclosed in JP-A-2006-247203. The case of acquiring a three-dimensional ultrasonic signal of the subject with the 1D array probe is included in the present embodiment.

The ultrasonic signal transmitting and receiving section drives the ultrasonic probe and transmits an ultrasonic signal to the subject and also receives a reflected echo signal from the subject and performs signal processing, such as amplification or phase adjustment, on the received reflected echo signal.

In addition, although the medical image processing method has been described in each embodiment, the medical image processing method may be considered as the invention of an operation method of a medical image diagnostic apparatus if an image acquisition step of acquiring a plurality of three-dimensional image data including a moving organ in each time phase is added.

In addition, in the explanation regarding the medical image processing method of each embodiment, the control unit is a computer and the operation is performed by a computer program. Therefore, it may be considered as the invention of a medical image processing program.

In addition, if an image acquisition function of acquiring a plurality of three-dimensional image data including a moving organ in each time phase is added to the medical image processing program, the result may be considered as the invention of an operation program of a medical image diagnostic apparatus.

INDUSTRIAL APPLICABILITY

The invention can be used for various kinds of medical image diagnostic apparatuses, such as an ultrasonic diagnostic apparatus, an X-ray CT apparatus, and an MRI apparatus. In addition, the invention may also be used for information apparatuses capable of performing image processing of an image obtained from a medical image diagnostic apparatus, such as a computer or various mobile terminals.

| Reference Signs List | |
|---|---|
| 1: | ultrasonic signal generating unit |
| 2: | ultrasonic image generating unit |
| 3: | calculation unit |
| 4: | storage unit |
| 5: | input unit |
| 6: | display unit |
| 7: | control unit |

The invention claimed is:

1. A medical image processing device comprising:
   an image input unit that inputs a plurality of three-dimensional image data including a moving organ in each time phase;
   a storage unit that stores the plurality of input three-dimensional image data;
   an image display unit that displays the stored three-dimensional image data as a three-dimensional image;
   an object-to-be-measured setting unit that sets a desired object to be measured on the three-dimensional image data stored in the storage unit by referring to the three-dimensional image displayed on the image display unit;
   a diagnostic index calculating unit that calculates a diagnostic index of the desired object to be measured from a diagnostic index of a reference object to be measured which is disposed near the desired object to be measured; and
   a control unit that performs control to display the calculated diagnostic index of the desired object to be measured on the image display unit,
   wherein the object-to-be-measured setting unit sets a plurality of reference objects to be measured, and the diagnostic index calculating unit calculates a plurality of diagnostic indexes based on the plurality of set reference objects to be measured and calculates the diagnostic index of the desired object to be measured by using the calculated plurality of diagnostic indexes.

2. The medical image processing device according to claim 1,
   wherein the control unit performs control to display the calculated diagnostic index and the three-dimensional image on the same screen of the image display unit.

3. The medical image processing device according to claim 1,
   wherein the control unit generates at least one two-dimensional image, which shows a desired two-dimensional section, from the three-dimensional image and performs control to display the generated two-dimensional image and the three-dimensional image and the diagnostic index on the same screen of the image display unit.

4. The medical image processing device according to claim 1,
   wherein the control unit converts the brightness or color of the three-dimensional image based on the calculated diagnostic index and performs control to display a three-dimensional image with the converted brightness or color on the image display unit.

5. The medical image processing device according to claim 1,
   wherein the diagnostic index calculating unit calculates the amount of displacement of the three-dimensional image data in each time phase for the desired object to be measured and calculates a diagnostic index based on the amount of displacement calculated in each time phase.

6. The medical image processing device according to claim 1,
   wherein the diagnostic index calculating unit calculates the diagnostic index of the desired object to be measured by a weighting operation on the plurality of calculated diagnostic indexes according to a distance from the desired object to be measured to each reference object to be measured.

7. The medical image processing device according to claim 6,
   wherein the object-to-be-measured setting unit sets the plurality of reference objects to be measured such that the desired object to be measured is interposed between the plurality of reference objects to be measured, and
   wherein the diagnostic index calculating unit performs an interpolation operation of the diagnostic index of the desired object to be measured based on diagnostic indexes of the plurality of set reference objects to be measured.

8. The medical image processing device according to claim 7,
   wherein the object-to-be-measured setting unit sets the desired object to be measured on the extension of a line segment passing through the plurality of reference objects to be measured, and
   wherein the diagnostic index calculating unit performs an extrapolation operation of the diagnostic index of the desired object to be measured based on diagnostic indexes of the plurality of set reference objects to be measured.

9. The medical image processing device according to claim 1, comprising:
   an amount of displacement calculating unit that calculates the amount of displacement of the desired object to be measured from a diagnostic index of a reference object to be measured which is disposed near the desired object to be measured,
   wherein the control unit performs control to display the calculated amount of displacement of the desired object to be measured on the image display unit.

10. The medical image processing device according to claim 9, comprising:

wherein the object-to-be-measured setting unit sets a plurality of reference objects to be measured, and wherein the amount of displacement calculating unit calculates a plurality of the amount of displacement based on the plurality of set reference objects to be measured and calculates the amount of displacement of the desired object to be measured by using the calculated plurality of the amount of displacement.

11. The medical image processing device according to claim 10, wherein the amount of displacement calculating unit calculates the amount of displacement of the desired object to be measured by weighting operation on the plurality of calculated amount of displacement according to a distance from the desired object to be measured to each reference object to be measured.

12. A medical image processing method comprising:
a first step of inputting a plurality of three-dimensional image data including a moving organ in each time phase by means of an image input unit;
a second step of storing the plurality of input three-dimensional image data in a storage unit;
a third step of displaying the stored three-dimensional image data as a three-dimensional image on a display unit;
a fourth step of setting a desired object to be measured on the three-dimensional image data stored in the storage unit by referring to the three-dimensional image displayed on the image display unit by means of an object-to-be-measured setting unit;
a fifth step of calculating a diagnostic index of the desired object to be measured from a diagnostic index of a reference object to be measured, which is disposed near the desired object to be measured, by means of a diagnostic index calculating unit; and
a sixth step of performing control to display the calculated diagnostic index of the desired object to be measured on the image display unit by means of a control unit, wherein the object-to-be-measured setting unit sets a plurality of reference objects to be measured, and the diagnostic index calculating unit calculates a plurality of diagnostic indexes based on the plurality of set reference objects to be measured and calculates the diagnostic index of the desired object to be measured by using the calculated plurality of diagnostic indexes.

13. The medical image processing method according to claim 12,
wherein the sixth step includes performing, by the control unit, control to display the calculated diagnostic index and the three-dimensional image on the same screen of the image display unit.

14. The medical image processing method according to claim 12,
wherein the sixth step includes performing, by the control unit, at least one two-dimensional image, which shows a desired two-dimensional section, from the three-dimensional image and performing control to display the generated two-dimensional image, the three-dimensional image, and the diagnostic index on the same screen of the image display unit.

15. The medical image processing method according to claim 12,
wherein the sixth step includes converting, by the control unit, the brightness or color of the three-dimensional image based on the calculated diagnostic index, and performing control to display a three-dimensional image with the converted brightness or color on the image display unit.

* * * * *